US009358063B2

(12) United States Patent
Marion

(10) Patent No.: US 9,358,063 B2
(45) Date of Patent: Jun. 7, 2016

(54) ABLATION PERFORMANCE INDICATOR FOR ELECTROSURGICAL DEVICES

(75) Inventor: Duane W. Marion, Santa Clara, CA (US)

(73) Assignee: ArthroCare Corporation, Austin, TX (US)

( * ) Notice: Subject to any disclaimer, the term of this patent is extended or adjusted under 35 U.S.C. 154(b) by 2178 days.

(21) Appl. No.: 12/031,231

(22) Filed: Feb. 14, 2008

(65) Prior Publication Data

US 2009/0209956 A1    Aug. 20, 2009

(51) Int. Cl.
*A61B 18/10*    (2006.01)
*A61B 18/12*    (2006.01)
*A61B 17/00*    (2006.01)
*A61B 18/00*    (2006.01)

(52) U.S. Cl.
CPC ... *A61B 18/1206* (2013.01); *A61B 2017/00115* (2013.01); *A61B 2018/00666* (2013.01); *A61B 2018/00827* (2013.01)

(58) Field of Classification Search
CPC .......... A61B 2018/00666; A61B 2018/00827; A61B 18/1206; A61B 18/1233; A61B 2018/00577; A61B 2018/00851; A61B 2018/00892; A61B 2018/1213; A61B 2017/00115
USPC ............................................... 606/34, 37–40
See application file for complete search history.

(56) References Cited

U.S. PATENT DOCUMENTS

| 2,050,904 A | 4/1936 | Trice ................................ 219/31 |
| 2,056,377 A | 10/1939 | Wappler ........................ 125/303 |
| 2,611,365 A | 9/1952 | Rubens ........................... 606/42 |
| 3,434,476 A | 3/1969 | Shaw et al. ...................... 606/22 |
| 3,633,425 A | 1/1972 | Sanford ........................... 73/356 |
| 3,707,149 A | 12/1972 | Hao et al. .................. 128/303.14 |
| 3,718,617 A | 2/1973 | Royal ........................... 260/30.4 |

(Continued)

FOREIGN PATENT DOCUMENTS

| DE | 3119735 | 1/1983 | ............. A61B 17/39 |
| DE | 3930451 A1 | 3/1991 | ............. A61B 17/39 |

(Continued)

OTHER PUBLICATIONS

Buchelt, et al. "Excimer Laser Ablation of Fibrocartilage: An In Vitro and In Vivo Study", Lasers in Surgery and Medicine, vol. 11, pp. 271-279, 1991.

(Continued)

*Primary Examiner* — Michael Peffley
*Assistant Examiner* — Samantha Good
(74) *Attorney, Agent, or Firm* — David A. Warmbold

(57) ABSTRACT

Ablation performance indicator for electrosurgical devices is described where ablation is typically characterized by the generation of a plasma discharge at the electrode assembly of an electrosurgical probe. When the electrode begins firing, the current waveform assumes a distinct appearance characterized by a spike at the leading edge of each half cycle followed by a lower level for the remaining period of the half cycle. A calculation of the waveform's Crest Factor can be used to determine the state at the electrode, e.g., whether the ablative energy is causing a desirable ablative effect on the electrode. This provides real-time measurements of the RMS and peak current amplitudes along with the Crest Factor and may also be used as limits or inputs to control algorithms or as inputs to indicate whether the device is in its ablative or non-ablative state.

16 Claims, 4 Drawing Sheets

(56) References Cited

U.S. PATENT DOCUMENTS

| | | | | |
|---|---|---|---|---|
| 3,815,604 | A | 6/1974 | O'Malley et al. | 128/305 |
| 3,828,780 | A | 8/1974 | Morrison, Jr. et al. | 128/275 |
| 3,901,242 | A | 8/1975 | Storz | 128/303 |
| 3,920,021 | A | 11/1975 | Hiltebrandt | 128/303 |
| 3,939,839 | A | 2/1976 | Curtiss | 128/303 |
| 3,963,030 | A | 6/1976 | Newton | 606/40 |
| 3,964,487 | A | 6/1976 | Judson | 606/39 |
| 3,970,088 | A | 7/1976 | Morrison | 128/303 |
| 4,033,351 | A | 7/1977 | Hetzel | 606/48 |
| 4,040,426 | A | 8/1977 | Morrison, Jr. | 128/303 |
| 4,043,342 | A | 8/1977 | Morrison, Jr. | 128/303 |
| 4,074,718 | A | 2/1978 | Morrison, Jr. | 128/303 |
| 4,092,986 | A | 6/1978 | Schneiderman | 128/303 |
| D249,549 | S | 9/1978 | Pike | D24/144 |
| 4,114,623 | A | 9/1978 | Meinke et al. | 606/39 |
| 4,116,198 | A | 9/1978 | Roos | 128/303 |
| 4,181,131 | A | 1/1980 | Ogiu | 128/303 |
| 4,184,492 | A | 1/1980 | Meinke et al. | 128/303 |
| 4,202,337 | A | 5/1980 | Hren et al. | 128/303 |
| 4,228,800 | A | 10/1980 | Degler, Jr. et al. | 128/303 |
| 4,232,676 | A | 11/1980 | Herczog | 128/303 |
| 4,240,441 | A | 12/1980 | Khalil | 600/505 |
| 4,248,231 | A | 2/1981 | Herczog et al. | 128/303 |
| 4,326,529 | A | 4/1982 | Doss et al. | 128/303 |
| 4,346,715 | A | 8/1982 | Gammell | 607/99 |
| 4,363,324 | A | 12/1982 | Kusserow | 607/64 |
| 4,378,801 | A | 4/1983 | Oosten | 606/37 |
| 4,381,007 | A | 4/1983 | Doss | 128/303 |
| 4,418,692 | A | 12/1983 | Guay | 606/42 |
| 4,474,179 | A | 10/1984 | Koch | 606/40 |
| 4,476,862 | A | 10/1984 | Pao | 128/303 |
| 4,509,532 | A | 4/1985 | DeVries | 128/736 |
| 4,532,924 | A | 8/1985 | Auth et al. | 128/303 |
| 4,548,207 | A | 10/1985 | Reimels | 128/303 |
| 4,567,890 | A | 2/1986 | Ohta et al. | 128/303 |
| 4,572,206 | A | 2/1986 | Geddes et al. | 600/505 |
| 4,580,557 | A | 4/1986 | Hertzmann | 606/12 |
| 4,587,975 | A | 5/1986 | Salo et al. | 600/506 |
| 4,590,934 | A | 5/1986 | Malis et al. | 128/303 |
| 4,593,691 | A | 6/1986 | Lindstrom et al. | 128/303 |
| 4,658,817 | A | 4/1987 | Hardy | 606/14 |
| 4,660,571 | A | 4/1987 | Hess et al. | 128/784 |
| 4,674,499 | A | 6/1987 | Pao | 128/303 |
| 4,682,596 | A | 7/1987 | Bales et al. | 128/303 |
| 4,706,667 | A | 11/1987 | Roos | 128/303 |
| 4,709,698 | A | 12/1987 | Johnston et al. | 606/41 |
| 4,727,874 | A | 3/1988 | Bowers et al. | 128/303 |
| 4,750,902 | A | 6/1988 | Wuchinich et al. | 604/22 |
| 4,765,331 | A | 8/1988 | Petruzzi et al. | 128/303 |
| 4,785,823 | A | 11/1988 | Eggers et al. | 128/692 |
| 4,805,616 | A | 2/1989 | Pao | 128/303 |
| 4,823,791 | A | 4/1989 | D'Amelio et al. | 123/303 |
| 4,832,048 | A | 5/1989 | Cohen | 128/786 |
| 4,846,179 | A | 7/1989 | O'Connor | 606/72 |
| 4,860,752 | A | 8/1989 | Turner | 607/102 |
| 4,907,589 | A | 3/1990 | Cosman | 606/34 |
| 4,920,978 | A | 5/1990 | Colvin | 128/784 |
| 4,931,047 | A | 6/1990 | Broadwin et al. | 604/22 |
| 4,936,281 | A | 6/1990 | Stasz | 128/660 |
| 4,936,301 | A | 6/1990 | Rexroth et al. | 606/45 |
| 4,943,290 | A | 7/1990 | Rexroth et al. | 606/45 |
| 4,955,377 | A | 9/1990 | Lennox et al. | 607/105 |
| 4,966,597 | A | 10/1990 | Cosman | 606/50 |
| 4,967,765 | A | 11/1990 | Turner et al. | 128/785 |
| 4,976,711 | A | 12/1990 | Parins et al. | 606/48 |
| 4,979,948 | A | 12/1990 | Geddes et al. | 606/33 |
| 4,998,933 | A | 3/1991 | Eggers et al. | 606/41 |
| 5,007,908 | A | 4/1991 | Rydell | 606/47 |
| 5,009,656 | A | 4/1991 | Reimels | 606/48 |
| 5,026,387 | A | 6/1991 | Thomas | 606/169 |
| 5,035,696 | A | 7/1991 | Rydell | 606/47 |
| 5,047,026 | A | 9/1991 | Rydell | 606/48 |
| 5,047,027 | A | 9/1991 | Rydell | 606/48 |
| 5,057,105 | A | 10/1991 | Malone et al. | 606/28 |
| 5,057,106 | A | 10/1991 | Kasevich et al. | 606/33 |
| 5,057,743 | A | 10/1991 | Krasko et al. | 313/639 |
| 5,078,717 | A | 1/1992 | Parins et al. | 606/48 |
| 5,080,660 | A | 1/1992 | Buelna | 606/45 |
| 5,083,565 | A | 1/1992 | Parins | 600/374 |
| 5,084,044 | A | 1/1992 | Quint | 606/27 |
| 5,085,659 | A | 2/1992 | Rydell | 606/47 |
| 5,086,401 | A | 2/1992 | Glassman et al. | 700/259 |
| 5,088,997 | A | 2/1992 | Delahuerga et al. | 606/42 |
| 5,092,339 | A | 3/1992 | Geddes et al. | 606/505 |
| 5,098,431 | A | 3/1992 | Rydell | 606/48 |
| 5,099,840 | A | 3/1992 | Goble | 128/422 |
| 5,102,410 | A | 4/1992 | Dressel | 606/15 |
| 5,108,391 | A | 4/1992 | Flachenecker et al. | 606/38 |
| RE33,925 | E | 5/1992 | Bales et al. | 606/48 |
| 5,112,330 | A | 5/1992 | Nishigaki et al. | 606/46 |
| 5,122,138 | A | 6/1992 | Manwaring | 606/46 |
| 5,125,928 | A | 6/1992 | Parins et al. | 606/48 |
| 5,156,151 | A | 10/1992 | Imran | 600/375 |
| 5,167,659 | A | 12/1992 | Ohtomo et al. | 606/40 |
| 5,171,311 | A | 12/1992 | Rydell et al. | 606/48 |
| 5,174,304 | A | 12/1992 | Latina et al. | 607/141 |
| 5,178,620 | A | 1/1993 | Eggers et al. | 606/41 |
| 5,183,338 | A | 2/1993 | Wickersheim et al. | 374/131 |
| 5,190,517 | A | 3/1993 | Zieve et al. | 604/22 |
| 5,192,280 | A | 3/1993 | Parins | 606/48 |
| 5,195,959 | A | 3/1993 | Smith | 604/34 |
| 5,197,466 | A | 3/1993 | Marchosky et al. | 128/399 |
| 5,197,963 | A | 3/1993 | Parins | 606/46 |
| 5,207,675 | A | 5/1993 | Canady | 606/40 |
| 5,217,457 | A | 6/1993 | Delahuerga et al. | 606/42 |
| 5,217,459 | A | 6/1993 | Kamerling | 606/48 |
| 5,249,585 | A | 10/1993 | Turner et al. | 607/99 |
| 5,255,980 | A | 10/1993 | Thomas et al. | 374/161 |
| 5,261,410 | A | 11/1993 | Alfano et al. | 600/475 |
| 5,267,994 | A | 12/1993 | Gentelia et al. | 606/15 |
| 5,267,997 | A | 12/1993 | Farin et al. | 606/38 |
| 5,273,524 | A | 12/1993 | Fox et al. | 604/21 |
| 5,277,201 | A | 1/1994 | Stern | 607/98 |
| 5,281,216 | A | 1/1994 | Klicek | 606/42 |
| 5,281,218 | A | 1/1994 | Imran | 606/41 |
| 5,282,799 | A | 2/1994 | Rydell | 606/48 |
| 5,290,282 | A | 3/1994 | Casscells | 606/29 |
| 5,300,069 | A | 4/1994 | Hunsberger et al. | 606/37 |
| 5,306,238 | A | 4/1994 | Fleenor | 606/42 |
| 5,312,400 | A | 5/1994 | Bales et al. | 606/41 |
| 5,314,406 | A | 5/1994 | Arias et al. | 604/21 |
| 5,318,563 | A | 6/1994 | Malis et al. | 606/38 |
| 5,324,254 | A | 6/1994 | Phillips | 604/21 |
| 5,330,470 | A | 7/1994 | Hagen | 606/42 |
| 5,334,140 | A | 8/1994 | Phillips | 604/35 |
| 5,334,183 | A | 8/1994 | Wuchinich | 606/46 |
| 5,334,193 | A | 8/1994 | Nardella | 606/41 |
| 5,336,172 | A | 8/1994 | Bales et al. | 604/27 |
| 5,336,220 | A | 8/1994 | Ryan et al. | 604/22 |
| 5,336,443 | A | 8/1994 | Odashima | 252/511 |
| 5,342,357 | A | 8/1994 | Nardella | 606/40 |
| 5,348,026 | A | 9/1994 | Davidson | 128/898 |
| 5,348,554 | A | 9/1994 | Imran et al. | 606/41 |
| 5,354,291 | A | 10/1994 | Bales et al. | 604/35 |
| 5,366,443 | A | 11/1994 | Eggers et al. | 604/114 |
| 5,370,675 | A | 12/1994 | Edwards et al. | 607/101 |
| 5,374,261 | A | 12/1994 | Yoon | 604/385.01 |
| 5,375,588 | A | 12/1994 | Yoon | 128/4 |
| 5,380,277 | A | 1/1995 | Phillips | 604/33 |
| 5,380,316 | A | 1/1995 | Aita | 606/7 |
| 5,383,874 | A | 1/1995 | Jackson et al. | 606/1 |
| 5,383,876 | A | 1/1995 | Nardella | 606/49 |
| 5,383,917 | A | 1/1995 | Desai et al. | 607/702 |
| 5,389,096 | A | 2/1995 | Aita | 606/15 |
| 5,395,312 | A | 3/1995 | Desai | 604/22 |
| 5,400,267 | A | 3/1995 | Denen et al. | 702/59 |
| 5,401,272 | A | 3/1995 | Perkins | 606/15 |
| 5,403,311 | A | 4/1995 | Abele et al. | 606/49 |
| 5,417,687 | A | 5/1995 | Nardella et al. | 606/32 |
| 5,419,767 | A | 5/1995 | Eggers et al. | 604/114 |
| 5,423,810 | A | 6/1995 | Goble et al. | 606/40 |
| 5,423,882 | A | 6/1995 | Jackman et al. | 607/122 |
| 5,436,566 | A | 7/1995 | Thompson et al. | 324/713 |
| 5,437,662 | A | 8/1995 | Nardella | 606/40 |

(56) References Cited

U.S. PATENT DOCUMENTS

| | | | |
|---|---|---|---|
| 5,438,302 A | 8/1995 | Goble | 331/167 |
| 5,441,499 A | 8/1995 | Fritzsch | 606/45 |
| 5,449,356 A | 9/1995 | Walbrink et al. | 606/49 |
| 5,451,224 A | 9/1995 | Goble et al. | 606/48 |
| 5,454,809 A | 10/1995 | Janssen | 606/41 |
| 5,458,596 A | 10/1995 | Lax et al. | 606/31 |
| 5,458,597 A | 10/1995 | Edwards et al. | 606/41 |
| 5,472,443 A | 12/1995 | Cordis et al. | 606/48 |
| 5,472,444 A | 12/1995 | Hueber et al. | 606/64 |
| 5,486,161 A | 1/1996 | Lax et al. | 604/22 |
| 5,496,312 A | 3/1996 | Klicek | 606/34 |
| 5,496,314 A | 3/1996 | Eggers | 606/41 |
| 5,496,317 A | 3/1996 | Goble et al. | 606/48 |
| 5,505,730 A | 4/1996 | Edwards et al. | 606/41 |
| 5,514,130 A | 5/1996 | Baker | 606/41 |
| 5,540,683 A | 7/1996 | Ichikawa et al. | 606/40 |
| 5,542,915 A | 8/1996 | Edwards et al. | 604/22 |
| 5,554,152 A | 9/1996 | Aita | 606/7 |
| 5,556,397 A | 9/1996 | Long et al. | 606/48 |
| 5,562,703 A | 10/1996 | Desai | 606/210 |
| 5,569,242 A | 10/1996 | Lax et al. | 606/42 |
| 5,571,100 A | 11/1996 | Goble et al. | 606/41 |
| 5,573,533 A | 11/1996 | Strul | 606/34 |
| 5,584,872 A | 12/1996 | LaFontaine et al. | 607/117 |
| 5,588,960 A | 12/1996 | Edwards et al. | 604/20 |
| 5,599,350 A | 2/1997 | Schulze et al. | 606/51 |
| 5,609,151 A | 3/1997 | Mulier et al. | 128/642 |
| 5,609,573 A | 3/1997 | Sandock | 604/22 |
| 5,633,578 A * | 5/1997 | Eggers et al. | 323/301 |
| 5,643,304 A | 7/1997 | Schechter et al. | 606/171 |
| 5,647,869 A | 7/1997 | Goble et al. | 606/37 |
| 5,658,278 A | 8/1997 | Imran et al. | 606/41 |
| 5,660,567 A | 8/1997 | Nierlich et al. | 439/620.21 |
| 5,662,680 A | 9/1997 | Desai | 606/210 |
| 5,676,693 A | 10/1997 | LaFontaine et al. | 607/116 |
| 5,681,282 A | 10/1997 | Eggers et al. | 604/114 |
| 5,683,366 A | 11/1997 | Eggers et al. | 604/114 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,697,925 A | 12/1997 | Taylor | 606/34 |
| 5,697,927 A | 12/1997 | Imran et al. | 606/41 |
| 5,700,262 A | 12/1997 | Acosta et al. | 606/48 |
| 5,715,817 A | 2/1998 | Stevens-Wright et al. | 600/373 |
| 5,722,975 A | 3/1998 | Edwards et al. | 606/41 |
| 5,725,524 A | 3/1998 | Mulier et al. | 606/41 |
| 5,749,869 A | 5/1998 | Lindenmeier et al. | 606/34 |
| 5,749,871 A | 5/1998 | Hood et al. | 606/50 |
| 5,749,914 A | 5/1998 | Janssen | 607/116 |
| 5,755,753 A | 5/1998 | Knowlton | 607/98 |
| 5,766,153 A | 6/1998 | Eggers et al. | 604/114 |
| 5,769,847 A | 6/1998 | Panescu et al. | 606/42 |
| 5,785,705 A | 7/1998 | Baker | 606/32 |
| 5,786,578 A | 7/1998 | Christy et al. | 219/720 |
| 5,800,429 A | 9/1998 | Edwards | 606/41 |
| 5,807,395 A | 9/1998 | Mulier et al. | 606/41 |
| 5,810,764 A | 9/1998 | Eggers et al. | 604/23 |
| 5,810,802 A | 9/1998 | Panescu et al. | 606/31 |
| 5,810,809 A | 9/1998 | Rydell | 606/49 |
| 5,836,875 A | 11/1998 | Webster, Jr. | 600/374 |
| 5,836,897 A | 11/1998 | Sakurai et al. | 601/2 |
| 5,843,019 A | 12/1998 | Eggers et al. | 604/22 |
| 5,860,951 A | 1/1999 | Eggers | 604/510 |
| 5,860,974 A | 1/1999 | Abele | 606/41 |
| 5,860,975 A | 1/1999 | Goble et al. | 606/45 |
| 5,871,469 A | 2/1999 | Eggers et al. | 604/114 |
| 5,873,855 A | 2/1999 | Eggers et al. | 604/114 |
| 5,873,877 A | 2/1999 | McGaffigan | 606/41 |
| 5,885,277 A | 3/1999 | Korth | 606/35 |
| 5,888,198 A | 3/1999 | Eggers et al. | 604/114 |
| 5,891,095 A | 4/1999 | Eggers et al. | 604/114 |
| 5,891,134 A | 4/1999 | Goble et al. | 606/27 |
| 5,897,553 A | 4/1999 | Mulier | 606/41 |
| 5,902,272 A | 5/1999 | Eggers et al. | 604/114 |
| 5,944,715 A | 8/1999 | Goble et al. | 606/41 |
| 5,954,716 A | 9/1999 | Sharkey et al. | 606/32 |
| 5,964,786 A | 10/1999 | Ochs et al. | 607/5 |
| 6,004,319 A | 12/1999 | Goble et al. | 606/48 |
| 6,013,076 A | 1/2000 | Goble et al. | 606/41 |
| 6,015,406 A | 1/2000 | Goble et al. | 606/41 |
| 6,024,733 A | 2/2000 | Eggers et al. | 604/500 |
| 6,027,501 A | 2/2000 | Goble et al. | 606/41 |
| 6,039,734 A | 3/2000 | Goble et al. | 606/41 |
| 6,047,700 A | 4/2000 | Eggers et al. | 128/898 |
| 6,056,746 A | 5/2000 | Goble et al. | 606/48 |
| 6,063,079 A | 5/2000 | Hovda et al. | 606/41 |
| 6,066,134 A | 5/2000 | Eggers et al. | 606/32 |
| 6,066,489 A | 5/2000 | Fields et al. | 435/236 |
| 6,068,628 A | 5/2000 | Fanton et al. | 606/41 |
| 6,074,386 A | 6/2000 | Goble et al. | 606/34 |
| 6,086,585 A | 7/2000 | Hovda et al. | 606/45 |
| 6,090,106 A | 7/2000 | Goble et al. | 606/41 |
| 6,090,107 A | 7/2000 | Borgmeier et al. | 606/41 |
| 6,093,186 A | 7/2000 | Goble et al. | 606/34 |
| 6,102,046 A | 8/2000 | Weinstein et al. | 128/898 |
| 6,103,298 A | 8/2000 | Edelson et al. | 427/77 |
| 6,105,581 A | 8/2000 | Eggers et al. | 128/898 |
| 6,109,268 A | 8/2000 | Thapliyal et al. | 128/898 |
| 6,117,109 A | 9/2000 | Eggers et al. | 604/114 |
| 6,126,682 A | 10/2000 | Sharkey et al. | 607/96 |
| 6,135,999 A | 10/2000 | Fanton et al. | 606/45 |
| 6,142,992 A | 11/2000 | Cheng et al. | 606/34 |
| 6,149,620 A | 11/2000 | Baker et al. | 604/22 |
| 6,156,334 A | 12/2000 | Meyer-Ingold et al. | 424/443 |
| 6,159,194 A | 12/2000 | Eggers et al. | 604/500 |
| 6,159,208 A | 12/2000 | Hovda et al. | 606/41 |
| 6,162,217 A | 12/2000 | Kannenberg et al. | 606/34 |
| 6,168,593 B1 | 1/2001 | Sharkey et al. | 606/34 |
| 6,174,309 B1 | 1/2001 | Wrublewski et al. | 606/45 |
| 6,179,824 B1 | 1/2001 | Eggers et al. | 604/500 |
| 6,179,836 B1 | 1/2001 | Eggers et al. | 606/45 |
| 6,183,469 B1 | 2/2001 | Thapliyal et al. | 606/41 |
| 6,190,381 B1 | 2/2001 | Olsen et al. | 606/32 |
| 6,197,021 B1 | 3/2001 | Panescu et al. | 606/31 |
| 6,203,542 B1 | 3/2001 | Ellsberry et al. | 606/41 |
| 6,210,402 B1 | 4/2001 | Olsen et al. | 606/32 |
| 6,210,405 B1 | 4/2001 | Goble et al. | 606/41 |
| 6,217,574 B1 | 4/2001 | Webster | 606/41 |
| 6,224,592 B1 | 5/2001 | Eggers et al. | 606/32 |
| 6,228,078 B1 | 5/2001 | Eggers | 606/32 |
| 6,228,081 B1 | 5/2001 | Goble | 606/34 |
| 6,234,178 B1 | 5/2001 | Goble et al. | 606/32 |
| 6,235,020 B1 | 5/2001 | Cheng et al. | 606/34 |
| 6,237,604 B1 | 5/2001 | Burnside et al. | 128/897 |
| 6,238,391 B1 | 5/2001 | Olsen et al. | 606/41 |
| 6,238,393 B1 | 5/2001 | Mulier et al. | 606/41 |
| 6,241,723 B1 * | 6/2001 | Heim et al. | 606/34 |
| 6,249,706 B1 | 6/2001 | Sobota et al. | 607/115 |
| 6,254,600 B1 | 7/2001 | Willink et al. | 606/41 |
| 6,258,087 B1 | 7/2001 | Edwards et al. | 606/41 |
| 6,261,286 B1 | 7/2001 | Goble et al. | 606/34 |
| 6,261,311 B1 | 7/2001 | Sharkey et al. | 607/96 |
| 6,264,652 B1 | 7/2001 | Eggers et al. | 606/41 |
| 6,270,460 B1 | 8/2001 | McCartan et al. | 600/459 |
| 6,277,112 B1 | 8/2001 | Underwood et al. | 606/32 |
| 6,280,441 B1 | 8/2001 | Ryan | 606/45 |
| 6,283,961 B1 | 9/2001 | Underwood et al. | 604/41 |
| 6,293,942 B1 | 9/2001 | Goble et al. | 606/38 |
| 6,296,636 B1 | 10/2001 | Cheng et al. | 606/32 |
| 6,296,638 B1 | 10/2001 | Davison et al. | 606/41 |
| 6,306,134 B1 | 10/2001 | Goble et al. | 606/42 |
| 6,308,089 B1 | 10/2001 | von der Rur et al. | 600/338 |
| 6,309,387 B1 | 10/2001 | Eggers et al. | 606/41 |
| 6,312,408 B1 | 11/2001 | Eggers et al. | 604/114 |
| 6,319,007 B1 | 11/2001 | Livaditis | 433/224 |
| 6,322,549 B1 | 11/2001 | Eggers et al. | 604/500 |
| 6,346,104 B2 | 2/2002 | Daly et al. | 606/34 |
| 6,346,107 B1 | 2/2002 | Cucin | 606/49 |
| 6,355,032 B1 | 3/2002 | Hovda et al. | 606/32 |
| 6,363,937 B1 | 4/2002 | Hovda et al. | 128/898 |
| 6,364,877 B1 | 4/2002 | Goble et al. | 606/34 |
| 6,379,350 B1 | 4/2002 | Sharkey et al. | 606/41 |
| 6,379,351 B1 | 4/2002 | Thapliyal et al. | 606/41 |

(56) References Cited

U.S. PATENT DOCUMENTS

| | | | |
|---|---|---|---|
| 6,391,025 B1 | 5/2002 | Weinstein et al. | 606/41 |
| 6,409,722 B1 | 6/2002 | Hoey et al. | 606/34 |
| 6,416,507 B1 | 7/2002 | Eggers et al. | 606/32 |
| 6,416,508 B1 | 7/2002 | Eggers et al. | 606/32 |
| 6,416,509 B1 | 7/2002 | Goble et al. | 606/37 |
| 6,425,912 B1 | 7/2002 | Knowlton | 607/101 |
| 6,432,103 B1 | 8/2002 | Ellsberry et al. | 606/41 |
| 6,440,129 B1 | 8/2002 | Simpson | 606/42 |
| 6,468,274 B1 | 10/2002 | Alleyne et al. | 606/32 |
| 6,468,275 B1 | 10/2002 | Wampler et al. | 606/48 |
| 6,482,201 B1 | 11/2002 | Olsen et al. | 606/41 |
| 6,500,173 B2 | 12/2002 | Underwood et al. | 606/32 |
| 6,514,248 B1 | 2/2003 | Eggers et al. | 606/41 |
| 6,514,250 B1 | 2/2003 | Jahns et al. | 606/41 |
| 6,517,498 B1 | 2/2003 | Burbank et al. | 600/564 |
| 6,530,922 B2 | 3/2003 | Cosman | 606/34 |
| 6,558,382 B2 | 5/2003 | Jahns et al. | 606/41 |
| 6,565,560 B1 | 5/2003 | Goble et al. | 606/41 |
| 6,578,579 B2 | 6/2003 | Burnside | 128/897 |
| 6,589,237 B2 | 7/2003 | Woloszko et al. | 606/41 |
| 6,602,248 B1 | 8/2003 | Sharps et al. | 606/32 |
| 6,620,156 B1 | 9/2003 | Garito et al. | 606/50 |
| 6,632,193 B1 | 10/2003 | Davison et al. | 604/22 |
| 6,632,220 B1 | 10/2003 | Eggers et al. | 606/41 |
| 6,635,034 B1 | 10/2003 | Cosmescu | 604/289 |
| 6,640,128 B2 | 10/2003 | Vilsmeier et al. | 600/427 |
| 6,656,177 B2 | 12/2003 | Truckai et al. | 606/51 |
| 6,663,554 B2 | 12/2003 | Babaev | 600/2 |
| 6,663,627 B2 | 12/2003 | Francischelli et al. | 606/41 |
| 6,702,810 B2 | 3/2004 | McClurken et al. | 606/34 |
| 6,730,080 B2 | 5/2004 | Harano et al. | 606/38 |
| 6,746,447 B2 | 6/2004 | Davison et al. | 606/41 |
| 6,749,604 B1 | 6/2004 | Eggers et al. | 606/41 |
| 6,749,608 B2 | 6/2004 | Garito et al. | 606/45 |
| D493,530 S | 7/2004 | Reschke | D24/144 |
| 6,770,071 B2 | 8/2004 | Woloszko et al. | 606/41 |
| 6,780,178 B2 | 8/2004 | Palanker et al. | 600/41 |
| 6,780,180 B1 | 8/2004 | Goble et al. | 606/41 |
| 6,780,184 B2 | 8/2004 | Tanrisever | 606/45 |
| 6,802,842 B2 | 10/2004 | Ellman et al. | 606/41 |
| 6,805,130 B2 | 10/2004 | Tasto et al. | 128/898 |
| 6,830,558 B2 | 12/2004 | Flaherty et al. | 604/67 |
| 6,837,887 B2 | 1/2005 | Woloszko et al. | 606/41 |
| 6,837,888 B2 | 1/2005 | Ciarrocca et al. | 606/41 |
| 6,855,143 B2 | 2/2005 | Davison et al. | 606/41 |
| 6,864,686 B2 | 3/2005 | Novak et al. | 324/419 |
| 6,866,671 B2 | 3/2005 | Tierney et al. | 606/130 |
| 6,872,183 B2 | 3/2005 | Sampson et al. | 600/561 |
| 6,878,149 B2 | 4/2005 | Gatto | 606/46 |
| 6,890,307 B2 | 5/2005 | Kokate et al. | 600/549 |
| 6,892,086 B2 | 5/2005 | Russell | 600/372 |
| 6,911,027 B1 | 6/2005 | Edwards et al. | 606/40 |
| 6,920,883 B2 | 7/2005 | Bessette et al. | 128/898 |
| 6,921,398 B2 | 7/2005 | Carmel et al. | 606/41 |
| 6,929,640 B1 | 8/2005 | Underwood et al. | 606/32 |
| 6,949,096 B2 | 9/2005 | Davison et al. | 606/41 |
| 6,953,461 B2 | 10/2005 | McClurken et al. | 606/51 |
| 6,960,204 B2 | 11/2005 | Eggers et al. | 606/32 |
| 6,974,453 B2 | 12/2005 | Woloszko et al. | 606/41 |
| 6,979,601 B2 | 12/2005 | Marr et al. | 438/132 |
| 6,984,231 B2 | 1/2006 | Goble et al. | 606/37 |
| 6,986,770 B2 | 1/2006 | Hood | 451/6 |
| 6,991,631 B2 | 1/2006 | Woloszko et al. | 606/41 |
| 7,001,382 B2 | 2/2006 | Gallo | 606/41 |
| 7,004,941 B2 | 2/2006 | Tvinnereim et al. | 606/41 |
| 7,010,353 B2 | 3/2006 | Gan et al. | 607/50 |
| 7,041,102 B2 | 5/2006 | Truckai et al. | 606/51 |
| 7,070,596 B1 | 7/2006 | Woloszko et al. | 606/41 |
| 7,090,672 B2 | 8/2006 | Underwood et al. | 606/41 |
| 7,094,215 B2 | 8/2006 | Davison et al. | 604/22 |
| 7,094,231 B1 | 8/2006 | Ellman et al. | 606/37 |
| 7,104,986 B2 | 9/2006 | Hovda et al. | 606/32 |
| 7,131,969 B1 | 11/2006 | Hovda et al. | 606/45 |
| 7,169,143 B2 | 1/2007 | Eggers et al. | 606/32 |
| 7,179,255 B2 | 2/2007 | Lettice et al. | 606/32 |
| 7,186,234 B2 | 3/2007 | Dahla et al. | 604/22 |
| 7,192,428 B2 | 3/2007 | Eggers et al. | 606/41 |
| 7,201,750 B1 | 4/2007 | Eggers et al. | 606/41 |
| 7,217,268 B2 | 5/2007 | Eggers et al. | 606/32 |
| 7,241,293 B2 | 7/2007 | Davison | 600/410 |
| 7,247,155 B2 | 7/2007 | Hoey et al. | 606/34 |
| 7,270,658 B2 | 9/2007 | Woloszko et al. | 606/32 |
| 7,270,659 B2 | 9/2007 | Hovda et al. | 606/32 |
| 7,270,661 B2 | 9/2007 | Dahla et al. | 606/41 |
| 7,271,363 B2 | 9/2007 | Lee et al. | 219/121.43 |
| 7,276,061 B2 | 10/2007 | Schaer et al. | 607/41 |
| 7,276,063 B2 | 10/2007 | Davison et al. | 606/45 |
| 7,278,994 B2 | 10/2007 | Goble | 606/41 |
| 7,282,048 B2 | 10/2007 | Goble et al. | 606/34 |
| 7,297,143 B2 | 11/2007 | Woloszko et al. | 606/41 |
| 7,297,145 B2 | 11/2007 | Ormsby et al. | 606/41 |
| 7,318,823 B2 | 1/2008 | Sharps et al. | 606/32 |
| 7,331,956 B2 | 2/2008 | Hovda et al. | 606/32 |
| RE40,156 E | 3/2008 | Sharps et al. | 606/32 |
| 7,344,532 B2 | 3/2008 | Goble et al. | 606/34 |
| 7,357,798 B2 | 4/2008 | Sharps et al. | 606/32 |
| 7,387,625 B2 | 6/2008 | Hovda et al. | 606/32 |
| 7,419,488 B2 | 9/2008 | Ciarrocca et al. | 606/41 |
| 7,429,260 B2 | 9/2008 | Underwood et al. | 606/32 |
| 7,429,262 B2 | 9/2008 | Woloszko et al. | 606/46 |
| 7,435,247 B2 | 10/2008 | Woloszko et al. | 604/45 |
| 7,527,624 B2 | 5/2009 | Dubnack et al. | 606/41 |
| 7,678,069 B1 | 3/2010 | Baker et al. | 604/22 |
| 7,691,101 B2 | 4/2010 | Davison et al. | 606/41 |
| 7,699,830 B2 | 4/2010 | Martin | 604/540 |
| 7,785,322 B2 | 8/2010 | Penny et al. | 606/34 |
| 7,824,398 B2 | 11/2010 | Woloszko et al. | 606/32 |
| 7,862,560 B2 | 1/2011 | Marion | 606/34 |
| 7,887,538 B2 | 2/2011 | Bleich et al. | 606/79 |
| 7,985,072 B2 | 7/2011 | Belikov et al. | 433/215 |
| D658,760 S | 5/2012 | Cox et al. | D24/144 |
| 8,192,424 B2 | 6/2012 | Woloszko | 606/40 |
| 8,303,583 B2 | 11/2012 | Hosier et al. | 606/48 |
| 8,568,405 B2 | 10/2013 | Cox et al. | 606/41 |
| 8,574,187 B2 | 11/2013 | Marion | 606/37 |
| 8,685,018 B2 | 4/2014 | Cox et al. | 606/41 |
| 8,747,399 B2 | 6/2014 | Woloszko et al. | 606/34 |
| 2001/0025177 A1 | 9/2001 | Woloszko et al. | 606/46 |
| 2002/0029036 A1 | 3/2002 | Goble et al. | 606/38 |
| 2002/0183739 A1 | 12/2002 | Long | 606/41 |
| 2003/0013986 A1 | 1/2003 | Saadat | 600/549 |
| 2003/0028189 A1 | 2/2003 | Woloszko et al. | 604/45 |
| 2003/0088245 A1 | 5/2003 | Woloszko et al. | 606/41 |
| 2003/0158545 A1 | 8/2003 | Hovda et al. | 606/32 |
| 2003/0167035 A1 | 9/2003 | Flaherty et al. | 604/67 |
| 2003/0171743 A1 | 9/2003 | Tasto et al. | 606/32 |
| 2003/0208194 A1 | 11/2003 | Hovda et al. | 606/41 |
| 2003/0208196 A1 | 11/2003 | Stone | 606/41 |
| 2003/0212396 A1 | 11/2003 | Eggers et al. | 606/41 |
| 2003/0216725 A1 | 11/2003 | Woloszko et al. | 60/41 |
| 2003/0216726 A1 | 11/2003 | Eggers et al. | 606/41 |
| 2003/0216732 A1 | 11/2003 | Truckai et al. | 606/49 |
| 2003/0232048 A1 | 12/2003 | Yang et al. | 424/141.1 |
| 2004/0030330 A1 | 2/2004 | Brassell et al. | 606/41 |
| 2004/0049180 A1 | 3/2004 | Sharps et al. | 606/32 |
| 2004/0058153 A1 | 3/2004 | Ren et al. | 428/408 |
| 2004/0092925 A1 | 5/2004 | Rizoiu et al. | 606/33 |
| 2004/0102044 A1 | 5/2004 | Mao et al. | 438/689 |
| 2004/0116922 A1 | 6/2004 | Hovda et al. | 606/41 |
| 2004/0127893 A1 | 7/2004 | Hovda | 606/41 |
| 2004/0186418 A1 | 9/2004 | Karashima | 604/20 |
| 2004/0230190 A1 | 11/2004 | Dahla et al. | 604/41 |
| 2005/0004634 A1 | 1/2005 | Hovda et al. | 606/41 |
| 2005/0010205 A1* | 1/2005 | Hovda et al. | 606/41 |
| 2005/0033278 A1 | 2/2005 | McClurken et al. | 606/34 |
| 2005/0119650 A1 | 6/2005 | Sanders et al. | 424/426 |
| 2005/0131402 A1 | 6/2005 | Ciarrocca et al. | 600/450 |
| 2005/0187543 A1 | 8/2005 | Underwood et al. | 606/41 |
| 2005/0197657 A1 | 9/2005 | Goth et al. | 606/41 |
| 2005/0234439 A1 | 10/2005 | Underwood et al. | 606/32 |
| 2005/0245923 A1 | 11/2005 | Christopherson et al. | 606/41 |
| 2005/0251134 A1 | 11/2005 | Woloszko et al. | 606/32 |
| 2005/0261754 A1 | 11/2005 | Woloszko et al. | 606/32 |
| 2005/0273091 A1 | 12/2005 | Booth et al. | 607/99 |

(56) References Cited

U.S. PATENT DOCUMENTS

| | | | |
|---|---|---|---|
| 2005/0288665 A1 | 12/2005 | Woloszko et al. | 606/41 |
| 2006/0036237 A1 | 2/2006 | Davison et al. | 606/41 |
| 2006/0095031 A1 | 5/2006 | Ormsby | 606/34 |
| 2006/0097615 A1 | 5/2006 | Tsakalakos et al. | 313/309 |
| 2006/0161148 A1* | 7/2006 | Behnke | 606/34 |
| 2006/0161150 A1* | 7/2006 | Keppel | 606/41 |
| 2006/0178670 A1 | 8/2006 | Woloszko et al. | 606/48 |
| 2006/0189971 A1 | 8/2006 | Eggers et al. | 606/32 |
| 2006/0253117 A1 | 11/2006 | Hovda et al. | 128/898 |
| 2006/0259025 A1 | 11/2006 | Dahla | 607/108 |
| 2007/0010808 A1 | 1/2007 | Dahla | 606/41 |
| 2007/0010809 A1 | 1/2007 | Sanders et al. | 606/32 |
| 2007/0093800 A1* | 4/2007 | Wham et al. | 606/34 |
| 2007/0106288 A1 | 5/2007 | Woloszko et al. | 606/41 |
| 2007/0112348 A1 | 5/2007 | Eggers et al. | 606/41 |
| 2007/0129715 A1 | 6/2007 | Eggers et al. | 606/32 |
| 2007/0149966 A1 | 6/2007 | Dahla et al. | 606/41 |
| 2007/0161981 A1 | 7/2007 | Sanders et al. | 606/41 |
| 2007/0179495 A1 | 8/2007 | Mitchell et al. | 606/41 |
| 2007/0179497 A1 | 8/2007 | Eggers et al. | 606/41 |
| 2007/0208334 A1 | 9/2007 | Woloszko et al. | 606/41 |
| 2007/0208335 A1 | 9/2007 | Woloszko et al. | 606/41 |
| 2007/0213700 A1 | 9/2007 | Davison et al. | 606/32 |
| 2007/0282323 A1 | 12/2007 | Woloszko et al. | 606/41 |
| 2008/0004615 A1 | 1/2008 | Woloszko et al. | 606/32 |
| 2008/0004621 A1 | 1/2008 | Dahla et al. | 606/48 |
| 2008/0077128 A1 | 3/2008 | Woloszko et al. | 606/41 |
| 2008/0138761 A1 | 6/2008 | Pond | 433/29 |
| 2008/0140069 A1 | 6/2008 | Filloux et al. | 606/41 |
| 2008/0154255 A1 | 6/2008 | Panos et al. | 606/33 |
| 2008/0167645 A1 | 7/2008 | Woloszko | 606/40 |
| 2008/0234674 A1 | 9/2008 | McClurken et al. | 606/50 |
| 2008/0243116 A1 | 10/2008 | Anderson | 606/41 |
| 2008/0261368 A1 | 10/2008 | Ramin et al. | 438/287 |
| 2008/0300590 A1 | 12/2008 | Horne et al. | 606/35 |
| 2009/0222001 A1 | 9/2009 | Greeley | 606/33 |
| 2010/0042101 A1 | 2/2010 | Inagaki et al. | 606/52 |
| 2010/0121317 A1 | 5/2010 | Lorang et al. | 606/41 |
| 2010/0152726 A1 | 6/2010 | Cadouri et al. | 606/41 |
| 2010/0228246 A1 | 9/2010 | Marion | 606/37 |
| 2010/0292689 A1 | 11/2010 | Davison et al. | 606/41 |
| 2010/0318083 A1 | 12/2010 | Davison et al. | 606/41 |
| 2010/0324549 A1 | 12/2010 | Marion | 606/37 |
| 2010/0331883 A1 | 12/2010 | Schmitz et al. | 606/249 |
| 2011/0137308 A1 | 6/2011 | Woloszko et al. | 606/41 |
| 2011/0208177 A1 | 8/2011 | Brannan | 606/33 |
| 2011/0245826 A1 | 10/2011 | Woloszko et al. | 606/41 |
| 2011/0270256 A1 | 11/2011 | Nelson et al. | 606/85 |
| 2011/0319887 A1 | 12/2011 | Keppel | 606/41 |
| 2012/0083782 A1 | 4/2012 | Stalder et al. | 606/41 |
| 2012/0095453 A1 | 4/2012 | Cox et al. | 606/33 |
| 2012/0095454 A1 | 4/2012 | Cox et al. | 606/33 |
| 2012/0109123 A1 | 5/2012 | Woloszko et al. | 606/45 |
| 2012/0196251 A1 | 8/2012 | Taft et al. | 433/216 |
| 2012/0197344 A1 | 8/2012 | Taft et al. | 607/51 |
| 2012/0215221 A1 | 8/2012 | Woloszko | 606/50 |
| 2012/0296328 A1 | 11/2012 | Marion | 606/34 |
| 2013/0116680 A1 | 5/2013 | Woloszko | 606/33 |
| 2014/0018798 A1 | 1/2014 | Cox et al. | 606/41 |
| 2014/0025065 A1 | 1/2014 | Marion | 606/33 |
| 2014/0135760 A1 | 5/2014 | Cadouri et al. | 606/41 |
| 2014/0155882 A1 | 6/2014 | Cox et al. | 606/34 |
| 2014/0236141 A1 | 8/2014 | Woloszko et al. | 606/34 |
| 2014/0257277 A1 | 9/2014 | Woloszko et al. | 606/41 |
| 2014/0257278 A1 | 9/2014 | Woloszko et al. | 606/41 |
| 2014/0257279 A1 | 9/2014 | Woloszko et al. | 606/41 |
| 2014/0276725 A1 | 9/2014 | Cox | 606/33 |
| 2015/0032101 A1 | 1/2015 | Woloszko et al. | 606/40 |

FOREIGN PATENT DOCUMENTS

| | | | |
|---|---|---|---|
| DE | 69635311 T2 | 4/2007 | A61B 18/12 |
| DE | 10201003288 | 9/2014 | A61B 18/12 |
| EP | 423757 | 3/1996 | A61B 17/39 |
| EP | 0703461 A2 | 3/1996 | G01B 27/02 |
| EP | 0740926 A2 | 11/1996 | A61B 17/39 |
| EP | 0 754 437 | 1/1997 | A61B 17/39 |
| EP | 0 694 290 | 11/2000 | A61B 18/04 |
| EP | 1334699 | 8/2003 | A61B 18/12 |
| EP | 1428480 | 6/2004 | A61B 18/12 |
| EP | 1707147 | 10/2006 | A61B 18/12 |
| EP | 2055254 | 1/2015 | A61B 18/12 |
| FR | 2313949 | 1/1977 | A61N 3/02 |
| GB | 467502 | 6/1937 | |
| GB | 2160102 | 12/1985 | A61B 17/38 |
| GB | 2299216 | 9/1996 | H01F 30/12 |
| GB | 2 308 979 | 7/1997 | A61B 17/36 |
| GB | 2 308 980 | 7/1997 | A61B 17/36 |
| GB | 2 308 981 | 7/1997 | A61B 17/36 |
| GB | 2 327 350 | 1/1999 | A61B 17/39 |
| GB | 2 327 351 | 1/1999 | A61B 17/39 |
| GB | 2 327 352 | 1/1999 | A61B 17/39 |
| GB | 2333455 | 7/1999 | G01K 11/12 |
| GB | 2406793 | 4/2005 | A61B 18/00 |
| GB | 2514442 | 11/2014 | A61B 18/14 |
| JP | 57-57802 | 4/1982 | A61B 1/00 |
| JP | 57-117843 | 7/1982 | A61B 17/39 |
| WO | 90/03152 | 4/1990 | A61B 17/39 |
| WO | 90/07303 | 7/1990 | A61B 17/39 |
| WO | 92/21278 | 12/1992 | A61B 5/04 |
| WO | 93/13816 | 7/1993 | A61B 17/36 |
| WO | 93/20747 | 10/1993 | A61B 5/00 |
| WO | 94/04220 | 3/1994 | |
| WO | 94/08654 | 4/1994 | A61M 37/00 |
| WO | 94/10921 | 5/1994 | A61B 18/00 |
| WO | 94/26228 | 11/1994 | A61B 18/14 |
| WO | 95/34259 | 12/1995 | A61F 5/48 |
| WO | 96/00040 | 1/1996 | A61B 18/00 |
| WO | 96/00042 | 1/1996 | A61B 17/39 |
| WO | 96/39086 | 12/1996 | A61B 18/12 |
| WO | 97/00646 | 1/1997 | A61B 17/39 |
| WO | 97/00647 | 1/1997 | A61B 17/39 |
| WO | 97/18768 | 5/1997 | A61B 17/39 |
| WO | 97/24073 | 7/1997 | A61B 17/39 |
| WO | 97/24074 | 7/1997 | A61B 17/39 |
| WO | 97/24993 | 7/1997 | A61B 17/39 |
| WO | 97/24994 | 7/1997 | A61B 17/39 |
| WO | 97/43971 | 11/1997 | A61B 17/39 |
| WO | 97/48345 | 12/1997 | A61B 17/39 |
| WO | 97/48346 | 12/1997 | A61B 17/39 |
| WO | 98/07468 | 2/1998 | A61N 1/40 |
| WO | 98/26724 | 6/1998 | A61B 17/36 |
| WO | 98/27879 | 7/1998 | A61B 17/36 |
| WO | 98/27880 | 7/1998 | A61B 17/39 |
| WO | 98/56324 | 12/1998 | A61F 7/12 |
| WO | 99/20213 | 4/1999 | A61F 7/12 |
| WO | 99/51155 | 10/1999 | A61B 17/36 |
| WO | 99/51158 | 10/1999 | A61B 17/39 |
| WO | 99/56648 | 11/1999 | A61B 17/39 |
| WO | 00/00098 | 1/2000 | A61B 17/36 |
| WO | 00/09053 | 2/2000 | A61F 7/12 |
| WO | 00/62685 | 10/2000 | A61B 17/20 |
| WO | 01/24720 | 4/2001 | A61B 18/18 |
| WO | 01/87154 | 5/2001 | A61B 5/05 |
| WO | 01/95819 | 12/2001 | A61B 18/14 |
| WO | 02/36028 | 5/2002 | A61B 18/12 |
| WO | 02/102255 | 12/2002 | A61B 17/20 |
| WO | 03/024305 | 3/2003 | |
| WO | 03/092477 | 11/2003 | |
| WO | 2004/026150 | 4/2004 | A61B 17/22 |
| WO | 2004/071278 | 8/2004 | |
| WO | 2005/125287 | 12/2005 | A61B 18/00 |
| WO | 2007/006000 | 1/2007 | A61B 18/14 |
| WO | 2007/056729 | 5/2007 | A61B 18/14 |
| WO | 2010/052717 | 5/2010 | A61B 18/14 |
| WO | 2012/050636 | 4/2012 | A61B 18/14 |
| WO | 2012/050637 | 4/2012 | A61B 18/14 |

OTHER PUBLICATIONS

Costello et al., "Nd: YAG Laser Ablation of the Prostate as a Treatment for Benign Prostatic Hypertrophy", Lasers in Surgery and Medicine, vol. 12, pp. 121-124, 1992.

(56) References Cited

OTHER PUBLICATIONS

Rand et al., "Effect of Elecctrocautery on Fresh Human Articular Cartilage", J. Arthro. Surg., vol. 1, pp. 242-246, 1985.
O'Neill et al., "Percutaneous Plasma Discectomy Stimulates Repair in Injured Porcine Intervertebral Discs", Dept. of Orthopaedic Surgery, Dept. of Radiology University of California at San Francisco, CA, 3 pgs.
PCT International Search Report for PCT/US99/14685), 1 pg Mailed Oct. 21, 1999.
PCT Notification of International Preliminary Examination Report for PCT/US99/14685, 4 pgs, Mailed Feb. 20, 2001.
PCT International Search Report for PCT/US98/22323, 1 pg, Mailed Mar. 3, 1999.
PCT Notification of International Preliminary Examination Report for PCT/US98/22323, 5 pgs, Mailed Nov. 28, 2000.
European Search Report for EP 98953859, 2 pgs, Jul. 2, 2001.
Supplementary European Search Report for EP 98953859, 3 pgs, Oct. 18, 2001.
PCT International Search Report for PCT/US99/18289, 1 pg, Mailed Dec. 7, 1999.
PCT Notification of International Preliminary Examination Report for PCT/US99/18289, 4 pgs, Mailed Jul. 7, 2000.
European Search Report for EP 99945039.8, 3 pgs, Oct. 1, 2001.
PCT International Search Report for PCT/US02/19261, 1 pg, Mailed Sep. 18, 2002.
PCT International Preliminary Examination Report for PCT/US02/19261, 3 pgs, Mar. 25, 2003.
PCT International Search Report for PCT/US02/29476, 1 pg, Mailed May 24, 2004.
PCT International Search Report for PCT/US03/13686, 1 pg, Mailed Nov. 25, 2003.
PCT International Search Report for PCT/USO4/03614, 1 pg, Mailed Sep. 14, 2004.
PCT Written Opinion of the International Searching Authority for PCT/US04/03614, 4 pgs, Mailed Sep. 14, 2004.
EP Communication, European Examination Report for EP 98953859.0, 3 pgs, Jun. 14, 2004.
EP Communication, European Examination Report for EP 99945039.8, 5 pgs, May 10, 2004.
PCT Notification of International Search Report and Written Opinion for PCT/US06/26321, 8pgs, Mailed Apr. 25, 2007.
PCT Notification of the International Search Report and Written Opinion for PCT/US06/60618, 7pgs, Mailed Oct. 5, 2007.
Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.
Codman & Shurtleff, Inc. "The Malis Bipolar Coagulating and Bipolar Cutting System CMC-II" brochure, early, 2 pgs, 1991.
Codman & Shurtleff, Inc. "The Malis Bipolar Electrosurgical System CMC-III Instruction Manual" , 15 pgs, Jul. 1991.
Cook et al., "Therapeutic Medical Devices: Application and Design" , Prentice Hall, Inc., 3pgs, 1982.
Dennis et al. "Evolution of Electrofulguration in Control of Bleeding of Experimental Gastric Ulcers," Digestive Diseases and Sciences, vol. 24, No. 11, 845-848, Nov. 1979.
Dobbie, A.K., "The Electrical Aspects of Surgical Diathermy, Bio Medical Engineering" *Bio-Medical Engineering* vol. 4, pp. 206-216, May 1969.
Elsasser, V.E. et al., "An Instrument for Transurethral Resection without Leakage of Current" *Acta Medicotechnica* vol. 24, No. 4, pp. 129-134, 1976.
Geddes, "Medical Device Accidents: With Illustrative Cases" CRC Press, 3 pgs, 1998.
Honig, W., "The Mechanism of Cutting in Electrosurgery" *IEEE* pp. 58-65, 1975.
Kramolowsky et al. "The Urological App of Electorsurgery" *J. of Urology* vol. 146, pp. 669-674, 1991.
Kramolowsky et al. "Use of 5F Bipolar Electrosurgical Probe in Endoscopic Urological Procedures" *J. of Urology* vol. 143, pp. 275-277, 1990.
Lee, B et al. "Thermal Compression and Molding of Artherosclerotic Vascular Tissue with Use" JACC vol. 13(5), pp. 1167-1171, 1989.
Letter from Department of Health to Jerry Malis dated Jan. 24, 1991, 3 pgs.
Letter from Department of Health to Jerry Malis dated Jul. 25, 1985, 1 pg.
Letter from Jerry Malis to FDA dated Jul. 25, 1985, 2 pgs.
Lu, et al., "Electrical Thermal Angioplasty: Catheter Design Features, In Vitro Tissue Ablation Studies and In Vitro Experimental Findings," *Am J. Cardiol* vol. 60, pp. 1117-1122, Nov. 1, 1987.
Malis, L., "Electrosurgery, Technical Note," *J. Neursurg.*, vol. 85, pp. 970-975, Nov. 1996.
Malis, L., "Excerpted from a seminar by Leonard I. Malis, M.D. at the 1995 American Association of Neurological Surgeons Meeting," 1pg, 1995.
Malis, L., "Instrumentation for Microvascular Neurosurgery" *Cerebrovascular Surgery*, vol. 1, pp. 245-260, 1985.
Malis, L., "New Trends in Microsurgery and Applied Technology," *Advanced Technology in Neurosurgery*, pp. 1-16, 1988.
Malis, L., "The Value of Irrigation During Bipolar Coagulation" See ARTC 21602, 1 pg, Apr. 9, 1993.
Nardella, P.C., *SPIE* 1068: pp. 42-49, Radio Frequency Energy and Impedance Feedback, 1989.
O'Malley, Schaum's Outline of Theory and Problems of Basic Circuit Analysis, McGraw-Hill, $2^{nd}$ Ed., pp. 3-5, 1992.
Olsen MD, Bipolar Laparoscopic Cholecstectomy Lecture (marked confidential), 12 pgs, Oct. 7, 1991.
Pearce, John A. "Electrosurgery", pp. 17, 69-75, 87, John Wiley & Sons, New York, 1986.
Pearce, John A., "Electrosurgery", Handbook of Biomedical Engineering, chapter 3, Academic Press Inc., N.Y., pp. 98-113, 1988.
Piercey et al., "Electrosurgical Treatment of Experimental Bleeding Canine Gastric Ulcers" *Gastroenterology* vol. 74(3), pp. 527-534, 1978.
Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455, 1981.
Ramsey et al., "A Comparison of Bipolar and Monopolar Diathermy Probes in Experimental Animals", *Urological Research* vol. 13, pp. 99-102, 1985.
Selikowitz et al., "Electric Current and Voltage Recordings on the Myocardium During Electrosurgical Procedures in Canines," *Surgery, Gynecology & Obstetrics*, vol. 164, pp. 219-224, Mar. 1987.
Shuman, "Bipolar Versus Monopolar Electrosurgery: Clinical Applications," *Dentistry Today*, vol. 20, No. 12, 7 pgs, Dec. 2001.
Slager et al. "Spark Erosion of Arteriosclerotic Plaques" *Z. Kardiol.* 76:Suppl. 6, pp. 67-71, 1987.
Slager et al. "Vaporization of Atherosclerotice Plaques by Spark Erosion" *JACC* 5(6): pp. 1382-1386, Jun. 1985.
Stoffels, E. et al., "Investigation on the Interaction Plasma-Bone Tissue", E-MRS Spring Meeting, 1 pg, Jun. 18-21, 2002.
Stoffels, E. et al., "Biomedical Applications of Plasmas", Tutorial presented prior to the $55^{th}$ Gaseous Electronics Conference in Minneapolis, MN, 41 pgs, Oct. 14, 2002.
Stoffels, E. et al., "Plasma Interactions with Living Cells", Eindhoven University of Technology, 1 pg, 2002.
Stoffels, E. et al., "Superficial Treatment of Mammalian Cells using Plasma Needle", J. Phys. D: Appl. Phys. 26, pp. 2908-2913, Nov. 19, 2003.
Stoffels, E. et al., "Plasma Needle", Eindhoven University of Technology, 1 pg, Nov. 28, 2003.
Stoffels, E. et al., "Plasma Physicists Move into Medicine", Physicsweb, 1 pg, Nov. 2003.
Stoffels, E. et al., "Plasma Treated Tissue Engineered Skin to Study Skin Damage", Biomechanics and Tissue Engineering, Materials Technology, 1 pg, 2003.
Stoffels, E. et al., "Plasma Treatment of Dental Cavities: A Feasibility Study", IEEE Transaction on Plasma Science, vol. 32, No. 4, pp. 1540-1542, Aug. 2004.

(56) References Cited

OTHER PUBLICATIONS

Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550 Aug. 2004.
Stoffels, E. et al., "Electrical and Optical Characterization of the Plasma Needle", New Journal of Physics 6, pp. 1-14, Oct. 28, 2004.
Stoffels, E. et al., "Where Plasma Meets Plasma", Eindhoven University of Technology, 23 pgs, 2004.
Stoffels, E. et al., "Gas Plasma effects on Living Cells", Physica Scripta, T107, pp. 79-82, 2004.
Stoffels, E. et al., "Plasma Treatment of Mammalian Vascular Cells: A Quantitative Description", IEEE Transaction on Plasma Science, vol. 33, No. 2, pp. 771-775, Apr. 2005.
Stoffels, E. et al., "Deactivation of *Escherichia coli* by the Plasma Needle", J. Phys. D: Appl. Phys. 38, pp. 1716-1721, May 20, 2005.
Stoffels, E. et al., "Development of a Gas Plasma Catheter for Gas Plasma Surgery", XXVIIth ICPIG, Endoven University of Technology, pp. 18-22, Jul. 2005.
Stoffels, E. et al., "Development of a Smart Positioning Sensor for the Plasma Needle", Plasma Sources Sci. Technol. 15, pp. 582-589, Jun. 27, 2006.
Stoffels, E. et al., Killing of S. Mutans Bacteria Using a Plasma Needle at Atmospheric Pressure, IEEE Transaction on Plasma Science, vol. 34, No. 4, pp. 1317-1324, Aug. 2006.
Stoffels, E. et al., "Plasma-Needle Treatment of Substrates with Respect to Wettability and Growth of *Excherichia coli* and *Streptococcus mutans*", IEEE Transaction on Plasma Science, vol. 34, No. 4, pp. 1325-1330, Aug. 2006.
Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.
Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.
Stoffels, E. et al., "Plasma Needle for In Vivo Medical Treatment: Recent Developments and Perspectives", Plasma Sources Sci. Technol. 15, pp. S169-S180, Oct. 6, 2006.
Swain, C.P., et al., "Which Electrode, A Comparison of four endoscopic methods of electrocoagulation in experimental bleeding ulcers" *Gut* vol. 25, pp. 1424-1431, 1987.
Tucker, R. et al. "A Comparison of Urologic Application of Bipolar Versus Monopolar Five French Electrosurgical Probes" *J. of Urology* vol. 141, pp. 662-665, 1989.
Tucker, R. et al. "In vivo effect of 5 French Bipolar and Monopolar Electrosurgical Probes on the Porcine Bladder" *Urological Research* vol. 18, pp. 291-294, 1990.
Tucker, R. et al., "Demodulated Low Frequency Currents from Electrosurgical Procedures," *Surgery, Gynecology and Obstetrics*, 159:39-43, 1984.
Tucker, R. et al., Abstract P14-11, p. 248, "A Bipolar Electrosurgical Turp Loop", Nov. 1989.
Valley Forge Scientific Corp., "Summary of Safety and Effective Information from 510K", 2pgs, 1991.
Valley Forge's New Products, CLINICA, 475, 5, Nov. 6, 1991.
Valleylab SSE2L Instruction Manual, 11 pgs, Jan. 6, 1983.
Valleylab, Inc. "Valleylab Part No. 945 100 102 A" Surgistat Service Manual, pp. 1-46, Jul. 1988.
Wattiez, Arnaud et al., "Electrosurgery in Operative Endoscopy," Electrosurgical Effects, Blackwell Science, pp. 85-93, 1995.
Wyeth, "Electrosurgical Unit" pp. 1181-1202, 2000.
UK Search Report for GB0805062.7 1 pg, Jul. 16, 2008.
BiLAP IFU 910033-002 Rev A for BiLAP Model 3527, L-Hook; BiLAP Model 3525, J-Hook; BiLAP Model 3529, High Angle, 2 pgs, Nov. 30, 1993.
BiLAP IFU 910026-001 Rev A for BiLAP Model 3525, J-Hook, 4 pgs, May 20, 1991.
BiLAP Generator Settings, Jun. 1991.
Tucker et al. "The interaction between electrosurgical generators, endroscopic electrodes, and tissue," Gastrointestinal Endoscopy, vol. 38, No. 2, pp. 118-122, 1992.
European Examination Report for EP 02749601.7 4pgs, Dec. 2, 2009.
European Examination Report 2 for EP 04708664 5pgs, May 3, 2010.
Extended European Search Report for EP09152846, 8pgs, Jan. 5, 2010.
European Search Report for EP 09152850, 2 pgs, Dec. 29, 2009.
European Examination Report for EP 02773432 4 pgs, Sep. 22, 2009.
European Examination Report for EP 05024974 4 pgs, Dec. 5, 2008.
European Examination Report for EP 04708664 7pgs, Sep. 7, 2009.
European Search Report for EP 02773432 3pgs, Dec. 19, 2008.
European Search Report for EP 04708664.0 5pgs, Apr. 6, 2009.
UK Search Report for GB0800129.9 2pgs, May 8, 2008.
UK Search Report for GB0900604.0 4 pgs, May 15, 2009.
UK Search Report for GB1110342.1 3pgs, Oct. 18, 2011.
uropean Examination Report (3rd) for EP 04708664 6pgs Nov. 6, 2012.
UK Suppl Search Report for GB1110342.1 2pgs Aug. 16, 2012.
UK Combined Search and Exam Report for GB1403997.8 5pgs Sep. 17, 2014.
Elgrabli, D., Abella-Gallart, S., Aguerre-Chariol, O., Robidel F.R., Boczkowski, J., Lacroix, G. (2007). Effect of BSA on carbon nanotube dispersion in vivi and in vitro studies. vol. 1, No. 4, pp. 266-278, 2007.
"Work functions for photoelectric effect". (2001). Retrieved on Jun. 11, 2014 from http://hyperphysics.phyastr.gsu.edu/hbase/tables/photoelec.html, 2001.
Jing et al. (2007). Biocompatibility of Cerium Oxide Films Synthesized by Dual Plasma Deposition. Key Enginerring Materials. vol. 330-332.pp. 749-752, 2007.
Wikipedia Field Electron Emission. Retrieved on Dec. 29, 2014 from http://en.wikipedia.org/wiki/Field_electron_emission.

\* cited by examiner

ABLATION PERFORMANCE INDICATOR FOR ELECTROSURGICAL DEVICES

FIELD OF THE INVENTION

The present invention relates to ablation performance indicators for electrosurgical devices. More particularly, the present invention relates to methods and apparatus for determining the ablative state of an electrosurgical device by measuring a wave shape of the current waveform.

BACKGROUND OF THE INVENTION

Electrosurgery typically utilizes the application of high frequency currents to cut or ablate tissue structures, either utilizing a monopolar or bipolar configuration. Monopolar configurations utilize an instrument having a single electrode and rely on external grounding of the patient whereas bipolar configurations utilize both an active and return electrode on the instrument itself for application of a current between the electrodes.

Electrosurgical procedures and techniques are particularly useful in reducing patient bleeding and trauma typically associated with surgical procedures. However, the radio frequency (RF) currents applied by electrosurgical instruments are typically controlled by utilizing control signals indicative of calculated root-mean-square (RMS) voltage and RMS current values. Generally, a current sensing transformer is used to measure the amount of RF current passing through the ablation electrode such that this measured current may be used to derive the RMS current via a signal converter which first squares the RF current input signal and then averages the squared signal over a prescribed period of time. The signal converter then calculates the square root of the average squared value to result in the RMS current. Accordingly, the RMS current signal may take the form of a relatively slowly varying signal compared to a rapidly varying RF current input signal.

Likewise, a voltage sensing transformer may be used to derive the RMS voltage via a RMS voltage converter which squares the RF voltage input signal and then averages it over the same prescribed period of time. The signal converter may then calculate the square root of the average squared voltage values to result in the RMS voltage. These RMS values may be used to control operation of the power supply to maintain the RF output voltage within a desired range or at a constant value or to control the power delivered through the ablation electrode. Such control thus allows for the physician to ablate or coagulate tissue in a controlled manner and may also serve as rudimentary inputs to control algorithms for other instruments.

However, utilization of these RMS values fails to consider the changes in wave shape of the applied voltage and current levels as the device enters different operating modes, particularly in thermal modes (non-ablative) and plasma modes (ablative) thus potentially resulting in the inaccurate application of voltage to the treated tissue.

SUMMARY OF THE INVENTION

Therefore, there is a need for determining the ablative state of an electrosurgical device by measuring a wave shape of the current waveform directly rather than utilizing calculated RMS values to accurately determine whether a device is in an ablative state or a non-ablative state. A system is described to characterize and measure the ablation performance at the electrode of an arthroscopic electrosurgical device. Utilizing RMS values alone in electrosurgical systems to control the delivery of a predetermined level of energy to a tissue region may fail to consider the changes in wave shape as the device enters different operating modes, e.g., thermal mode (non-ablative) and plasma mode (ablative).

As discussed herein, ablation is characterized by the generation of a plasma discharge at the electrode assembly of an electrosurgical probe, the typical voltage waveform is a square waveform and utilization of such plasma to dissociate portions of a target tissue. The measured current waveform may typically approximate a square waveform when the electrosurgical system is operated in the thermal mode, as during an initial period before the plasma mode becomes active, where the current waveform roughly approximates the shape of the square voltage waveform. However, when plasma discharge is initiated and the electrode assembly begins to discharge the current waveform takes on a distinctly different appearance where the current is characterized by a spike at the leading edge of each half cycle followed by a much lower level for the remaining period of the half cycle.

The present system and method preferably discerns a difference between the two wave shapes, e.g., between the signal's initial square waveform (when the system is in the thermal mode) and a spiked waveform (when the system is in the plasma mode) by considering their Crest Factor, C, which for a waveform is defined as $C = X_{PEAK}/X_{RMS}$, where $X_{PEAK}$ is the peak amplitude of the waveform and $X_{RMS}$ is the RMS or time-averaged value of the waveform over a specified time interval. The Crest Factor may also be defined as the peak-to-average ratio. As a current load is applied such as during an ablative state, the wave shape deviates farther from a square waveform and the Crest Factor increases. For instance, when ablation is active and the system is in the plasma mode, the Crest Factor of the current waveform is several times the value when the ablative state is not active.

A measurement of the Crest Factor can therefore be used to make a determination of the state at the electrode, e.g., whether the applied energy is causing a desirable ablative effect on the electrode. This method may provide real-time measurements of the RMS and peak current amplitudes along with the Crest Factor. Moreover, these parameters may be used as limits or inputs to control algorithms or as inputs into a mechanism to indicate to a user whether the device was in its ablative or non-ablative state.

The present disclosure includes a number of important technical advantages. One technical advantage is the provision of a circuit designed to determine whether an electrode is in an ablative or non-ablative state. Another technical advantage is the provision of an ablation performance indicator on an electrosurgical instrument. Additional advantages will be apparent to those of skill in the art and from the figures, description and claims provided herein.

DETAILED DESCRIPTION OF THE INVENTION

Figure 1:
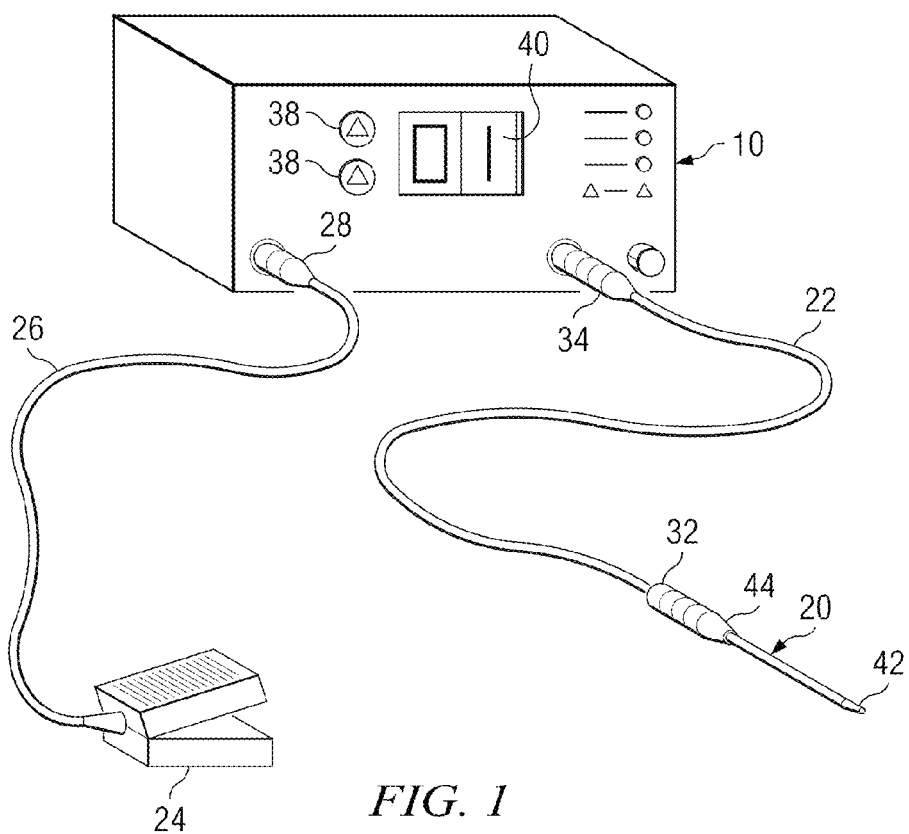
FIG. 1 shows an exemplary electrosurgical system for an instrument configured to treat various tissue regions.

As discussed herein, ablation is characterized by the generation of a plasma discharge at the electrode assembly of an electrosurgical probe, the typical voltage waveform is a square waveform and utilization of such plasma to dissociate portions of a target tissue. In other words, as discussed herein, the term 'ablation' shall mean the removal, cutting, or resection of target tissue in which a plasma discharge or plasma field developed proximate an active electrode assembly substantially effects such removal, cutting or resection. Further, ablation shall not mean the removal, cutting or resection of tissue where no significant plasma or plasma field is developed and where the primary means for effecting the removal, cutting or resection is by passing current directly through the tissue (e.g. a Bovie device). As ablation is typically characterized by the generation of a plasma discharge at the electrode assembly of an electrosurgical probe, the typical measured current waveform may approximate a square waveform prior to the plasma mode being entered, while the system is still in the thermal mode. However, when plasma discharge is initiated and the electrode assembly begins firing, the current waveform takes on a distinctly different appearance where the current is generally characterized by a spike at the leading edge of each half cycle followed by a substantially lower level for the remaining period of the half cycle.

As described herein, the Crest Factor, C, is preferably used to discern a difference between the two wave shapes, e.g., between the signal's initial square waveform (prior to the initiation of the plasma mode) and a spiked waveform (when the ablation is active). When the electrosurgical system enters the ablative state, the wave shape deviates from a square waveform and the Crest Factor increases. A measurement of the Crest Factor can therefore be used to make a determination of the state at the electrode, e.g., whether the ablative energy is causing a desirable ablative effect on the electrode. This method may preferably provide real-time measurements of the RMS and peak current amplitudes along with the Crest Factor. Moreover, these parameters may be used as limits or inputs to control algorithms or as inputs into a mechanism to indicate to a user whether the device was in its ablative or non-ablative state.

In many electrosurgical procedures, a high frequency voltage difference is applied between the active electrode(s) and one or more return electrode(s) to develop high electric field intensities in the vicinity of the target tissue site. The high electric field intensities lead to electric field induced molecular breakdown of target tissue through molecular dissociation (rather than thermal evaporation or carbonization). This molecular disintegration completely removes the tissue structure, as opposed to dehydrating the tissue material by the removal of liquid from within the cells of the tissue, as is typically the case with electrosurgical desiccation and vaporization.

The high electric field intensities may be generated by applying a high frequency voltage that is sufficient to vaporize an electrically conductive fluid over at least a portion of the active electrode(s) in the region between the distal tip of the active electrode(s) and the target tissue. The electrically conductive fluid may be a gas or liquid, such as isotonic saline, delivered to the target site, or a viscous fluid, such as a gel, that is located at the target site. In the latter embodiment, the active electrode(s) are submersed in the electrically conductive gel during the surgical procedure. Since the vapor layer or vaporized region has relatively high electrical impedance, it minimizes the current flow into the electrically conductive fluid. This ionization, under optimal conditions, induces the discharge of energetic electrons and photons from the vapor layer to the surface of the target tissue. A more detailed description of this cold ablation phenomenon, termed Coblation®, can be found in commonly assigned U.S. Pat. No. 5,683,366 the complete disclosure of which is incorporated herein by reference in its entirety.

The systems and methods for selectively applying electrical energy to a target location within or on a patient's body may be accomplished particularly in procedures where the tissue site is fully or partially flooded or submerged with an electrically conductive fluid, such as during arthroscopic surgery of the knee, shoulder, ankle, hip, elbow, hand, foot, etc. Other tissue regions which may be treated by the system and methods described herein may also include, but are not limited to, prostate tissue, and leiomyomas (fibroids) located within the uterus, gingival tissues and mucosal tissues located in the mouth, tumors, scar tissue, myocardial tissue, collagenous tissue within the eye or epidermal and dermal tissues on the surface of the skin, etc. and may be used in the presence of an electrically conductive gel or where sufficient electrically conductive fluid is available (either delivered to the target site or naturally occurring at the target site). Other procedures which may be performed may also include laminectomy/disketomy procedures for treating herniated disks, decompressive laminectomy for stenosis in the lumbosacral and cervical spine, posterior lumbosacral and cervical spine fusions, treatment of scoliosis associated with vertebral disease, foraminotomies to remove the roof of the intervertebral foramina to relieve nerve root compression, as well as anterior cervical and lumbar diskectomies. Tissue resection within accessible sites of the body that are suitable for electrode loop resection, such as the resection of prostate tissue, leiomyomas (fibroids) located within the uterus, and other diseased tissue within the body, may also be performed.

Other procedures which may be performed where multiple tissue types are present may also include, e.g., the resection and/or ablation of the meniscus and the synovial tissue within a joint during an arthroscopic procedure. It will be appreciated that the systems and methods described herein can be applied equally well to procedures involving other tissues of the body, as well as to other procedures including open procedures, intravascular procedures, urology, laparoscopy, arthroscopy, thoracoscopy or other cardiac procedures, dermatology, orthopedics, gynecology, otorhinolaryngology, spinal and neurologic procedures, oncology, and the like.

The electrosurgical instrument may comprise a shaft or a handpiece having a proximal end and a distal end which supports the one or more active electrodes. The shaft or handpiece may assume a wide variety of configurations, with the primary purpose being to mechanically support the active electrode and permit the treating physician to manipulate the electrodes from a proximal end of the shaft. The shaft may be rigid or flexible, with flexible shafts optionally being combined with a generally rigid external tube for mechanical support. The distal portion of the shaft may comprise a flexible material, such as plastics, malleable stainless steel, etc, so that the physician can mold the shaft and/or distal portion in a desired configuration for a particular application. Flexible shafts may be combined with pull wires, shape memory actuators, and other known mechanisms for effecting selective deflection of the distal end of the shaft to facilitate positioning of the electrode array. The shaft will usually include a plurality of wires or other conductive elements running axially therethrough to permit connection of the electrode array to a connector at the proximal end of the shaft. Thus, the shaft may typically have a length between at least 5 cm and at least 10 cm, more typically being 20 cm or longer for endoscopic procedures. The shaft may typically have a diameter of at least 0.5 mm and frequently in the range of from about 1 mm to 10 mm. Of course, in various procedures, the shaft may have any suitable length and diameter that would facilitate handling by the surgeon.

As mentioned above, a gas or fluid is typically applied to the target tissue region and in some procedures it may also be desirable to retrieve or aspirate the electrically conductive fluid after it has been directed to the target site. In addition, it may be desirable to aspirate small pieces of tissue that are not completely disintegrated by the high frequency energy, air bubbles, or other fluids at the target site, such as blood, mucus, the gaseous products of ablation, etc. Accordingly, the instruments described herein can include a suction lumen in the probe or on another instrument for aspirating fluids from the target site.

Referring to FIG. 1, an exemplary electrosurgical system for a single instrument having multiple electrodes configured to treat varying tissue regions is illustrated in the assembly. As shown, the electrosurgical system may generally comprise an electrosurgical probe 20 connected to a power supply 10 for providing high frequency voltage to the active electrodes. Probe 20 includes a connector housing 44 at its proximal end, which may be either permanently or removably connected to a probe receptacle 32 of a probe cable 22. The proximal portion of cable 22 has a connector 34 to couple probe 20 to power supply 10 to power the one or more electrodes of electrode assembly 42 positioned near or at the distal end of probe 20.

Power supply 10 has an operator controllable voltage level adjustment 38 to change the applied voltage level, which is observable at a voltage level display 40. Power supply 10 may also include one or more foot pedals 24 and a cable 26 which is removably coupled to a receptacle with a cable connector 28. The foot pedal 24 may also include a second pedal (not shown) for remotely adjusting the energy level applied to the active electrodes and a third pedal (also not shown) for switching between an ablation mode and a coagulation mode or for switching to activate between electrodes. In alternative embodiments (not expressly shown) probe 20 may include one or more control switches for activating the ablation or coagulation output and adjusting the energy level applied to the active electrodes. Operation of and configurations for the power supply 10 are described in further detail in U.S. Pat. No. 6,746,447, which is incorporated herein by reference in its entirety.

The voltage applied between the return electrodes and the active electrodes may be at high or radio frequency, typically between about 5 kHz and 20 MHz, usually being between about 30 kHz and 2.5 MHz, preferably being between about 50 kHz and 500 kHz, more preferably less than 350 kHz, and most preferably between about 100 kHz and 200 kHz. The RMS (root mean square) voltage applied will usually be in the range from about 5 volts to 1000 volts, preferably being in the range from about 10 volts to 500 volts depending on the active electrode size, the operating frequency and the operation mode of the particular procedure or desired effect on the tissue (i.e., contraction, coagulation or ablation). Typically, the peak-to-peak voltage will be in the range of 10 to 2000 volts, preferably in the range of 20 to 1200 volts and more preferably in the range of about 40 to 800 volts (again, depending on the electrode size, the operating frequency and the operation mode).

The power source may be current limited or otherwise controlled so that undesired heating of the target tissue or surrounding (non-target) tissue does not occur. In one variation, current limiting inductors are placed in series with each independent active electrode, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in PCT application WO 94/026228, which is incorporated herein by reference in its entirety.

Additionally, current limiting resistors may be selected. These resistors will have a large positive temperature coefficient of resistance so that, as the current level begins to rise for any individual active electrode in contact with a low resistance medium (e.g., saline irrigant or conductive gel), the resistance of the current limiting resistor increases significantly, thereby minimizing the power delivery from the active electrode into the low resistance medium (e.g., saline irrigant or conductive gel).

Figure 2:
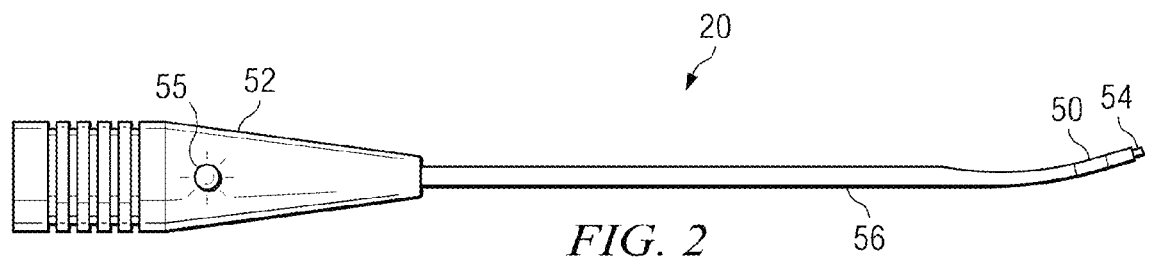
FIG. 2 illustrates an exemplary electrosurgical probe which generally includes an elongated shaft which may be flexible or rigid, a handle coupled to the proximal end of shaft and a multi-electrode assembly.

FIG. 2 illustrates an exemplary electrosurgical probe 20 which generally includes an elongate shaft 50 which may be flexible or rigid, a handle 52 coupled to the proximal end of shaft 50 and an electrode assembly 54, described in further detail below, coupled to the distal end of shaft 50. Shaft 50 may comprise an electrically conducting material, such as metal, which may be selected from the group consisting of, e.g., tungsten, stainless steel alloys, platinum or its alloys, titanium or its alloys, molybdenum or its alloys, and nickel or its alloys. Shaft 50 also includes an electrically insulating jacket 56, which is typically formed as one or more electrically insulating sheaths or coatings, such as polytetrafluoroethylene, polyimide, and the like. The provision of the electrically insulating jacket over the shaft prevents direct electrical contact between these conductive elements and any adjacent body structure or the user One or more lumens (not expressly shown) may be formed within or along shaft 50 and terminate in openings at the distal end of shaft 50 to deliver fluid or provide suction proximate electrode assembly 54. Such lumens may also pass through handle 52 to allow for fluid communication with a suitable fluid source or suction/vacuum source.

Handle 52 typically comprises a plastic material that is easily molded into a suitable shape for handling by the surgeon. Moreover, the distal portion of shaft 50 may be bent to improve access to the operative site of the tissue being treated. In alternative embodiments, the distal portion of shaft 50 comprises a flexible material which can be deflected relative to the longitudinal axis of the shaft. Such deflection may be selectively induced by mechanical tension of a pull wire, for example, or by a shape memory wire that expands or contracts by externally applied temperature changes. A more complete description of this embodiment can be found in PCT application WO 94/026228, which has been incorporated by reference above.

The bend in the distal portion of shaft 50 is particularly advantageous in arthroscopic treatment of joint tissue as it allows the surgeon to reach the target tissue within the joint as the shaft 50 extends through a cannula or portal. Of course, it will be recognized that the shaft may have different angles depending on a particular treatment application. For example, a shaft having a 90° bend angle may be particularly useful for accessing tissue located in the back portion of a joint compartment and a shaft having a 10° to 30° bend angle may be useful for accessing tissue near or in the front portion of the joint compartment.

Regardless of the bend angle, an electrode assembly having multiple, e.g., two or more, electrodes disposed near or at the distal end of shaft 50 may be utilized. One difficulty in designing electrosurgical devices with relatively large active electrodes is that a relatively high level of RF energy is delivered before ablative effects are activated at the electrodes. However, once the ablative effects are activated, the load impedance increases and the power delivery to the tissue decreases. In some embodiments a multi-electrode assembly may be configured to more effectively deliver the energy to a tissue region of interest, for instance, less energy may be required than if a single electrode with the same overall effective surface area were used. In such embodiments the multiple electrodes may effectively serve to "diffuse" the same amount of energy over a larger area.

Power supply 10 as described in the present system above as well as other electrosurgical systems may be controlled to deliver a predetermined level of energy to a tissue region to be treated. This may utilize limiting the applied current or voltage so that undesired heating of the target tissue or surrounding (non-target) tissue does not occur. Utilizing RMS values alone fails to consider the changes in wave shape as the device enters different operating modes, particularly in thermal mode (non-ablative) and plasma mode (ablative).

Probe 20 further includes performance indicator 55. Performance indicator 55 may include one or more LEDs or similar indicators in electrical communication with circuit 90. As circuit 90 determines that probe 20 is an ablative or non-ablative state based on Crest Factor C, indicator 55 may be illuminated to provide the user a visual indication of whether an ablative or non-ablative state is detected. In an alternative embodiment an indicator (not expressly shown) may be disposed within power supply 10 either in addition to or in place of indicator 55. Additionally, such an indicator provided in the power supply may also provide an audible tone or similar audible signal to indicate the detected state to the user.

Figure 3:
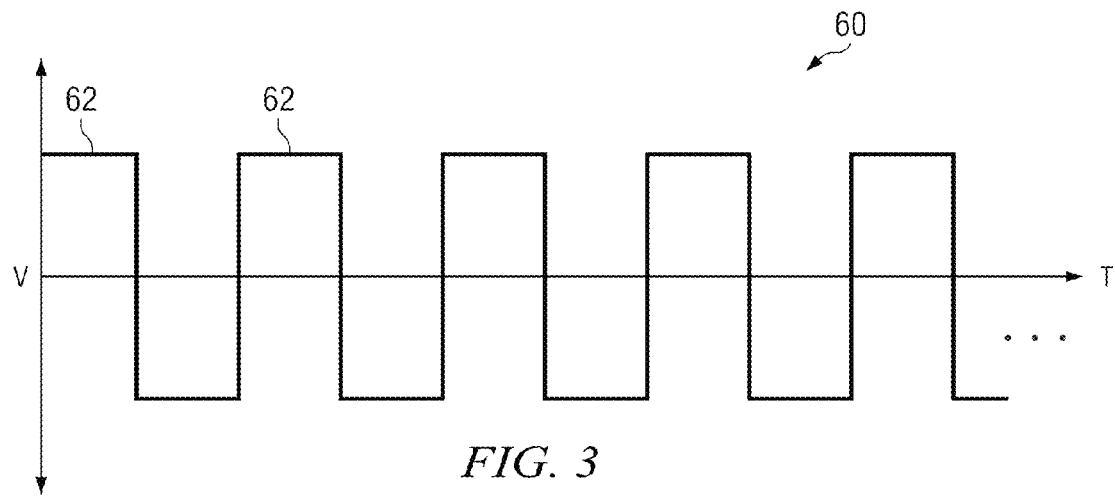
FIG. 3 shows a typical square waveform of an applied voltage.
Figure 4:
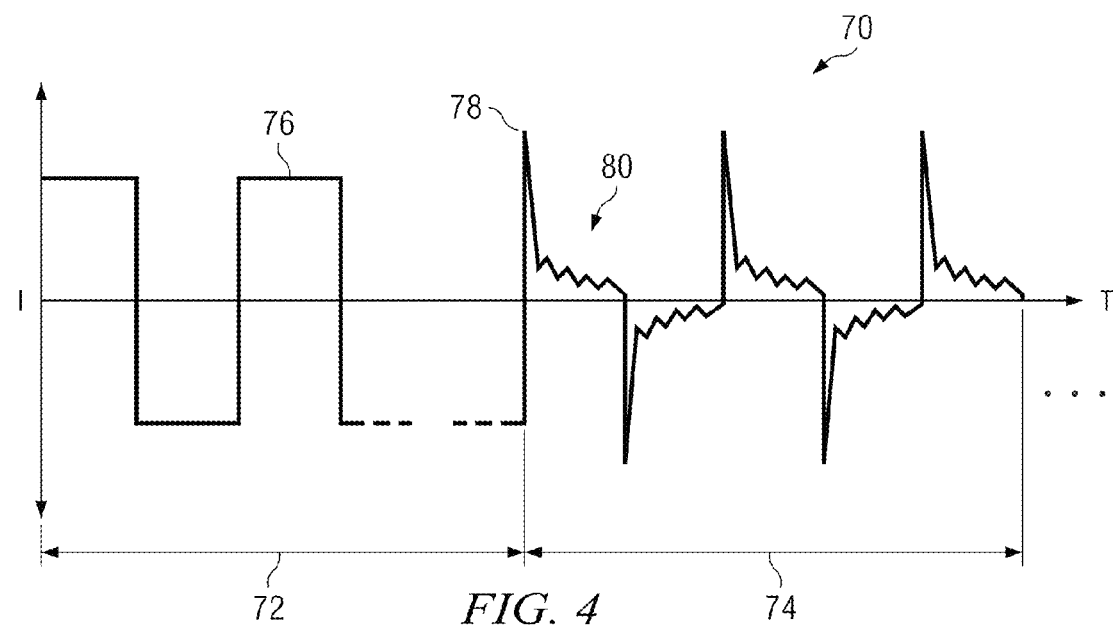
FIG. 4 illustrates an example of a current waveform approximating a square waveform when ablation is inactive and the subsequent spiked waveform resulting from the activation of ablation.

As discussed herein, ablation is typically characterized by the generation of a plasma discharge at the electrode assembly 54 of the electrosurgical probe 20. The typical voltage waveform is illustrated in plot 60 which shows square waveform 62 in FIG. 3. The measured current waveform 70, as illustrated in FIG. 4, illustrates an initial square waveform 76 when the electrosurgical system is operating in the thermal mode, as during initial period 72. The square current waveform 76 roughly approximates the shape of the voltage waveform 62 illustrated above as the applied load is purely resistive. However, when plasma discharge is initiated and electrode assembly 54 begins firing, the current waveform takes on a distinctly different appearance, as indicated during the period of active ablation 74. During this period of active ablation, the current is characterized by a spike 78 at the leading edge of each half cycle followed by a much lower level 80 for the remaining period of the half cycle.

As described herein, waveform 70 is preferably analyzed to discern a difference between the two wave shapes, e.g., between the signal's initial square waveform 76 (when the system is in the thermal mode 72) and spiked waveform 78 (when the system is in the plasma mode 74). The difference between the two waveforms may be discerned by considering their Crest Factor, C, which for a waveform is defined as:

$$C = \frac{X_{PEAK}}{X_{RMS}} \quad (1)$$

where $X_{PEAK}$ is the peak amplitude of the waveform and $X_{RMS}$ is the RMS or time-averaged value of the waveform over a specified time interval. The Crest Factor is sometimes also defined as the peak-to-average ratio. When the system is in the thermal mode during an initial non-ablative period 72, the current waveform is square and the Crest Factor is 1 where the peak amplitude and RMS values are equal, e.g., square waveform 76. Once the system begins operating in the plasma mode, such as during ablative state 74, the wave shape deviates farther from a square waveform and the Crest Factor increases, e.g., spiked waveform 78. For instance, when ablation is active 74 the Crest Factor of the current waveform is several times the value when it is not active 72.

When an electrosurgical device, e.g., an arthroscopic ablation instrument, enters an ablative state the waveform is typically characterized by a relatively high leading edge or spike 78, followed by a much lower level 80 for the remaining half cycle resulting in a high Crest Factor since its peak is much higher than its RMS value. A measurement of the Crest Factor can therefore be used to make a determination of the state at the electrode, e.g., whether the ablative energy is causing a desirable ablative effect (for example, creating a plasma) proximate the electrode. This method may provide real-time measurements of the RMS and peak current amplitudes along with the Crest Factor. Moreover, these parameters may be used as limits or inputs to control algorithms or as inputs into a mechanism to indicate to a user whether the device was in its ablative or non-ablative state.

Figure 5:
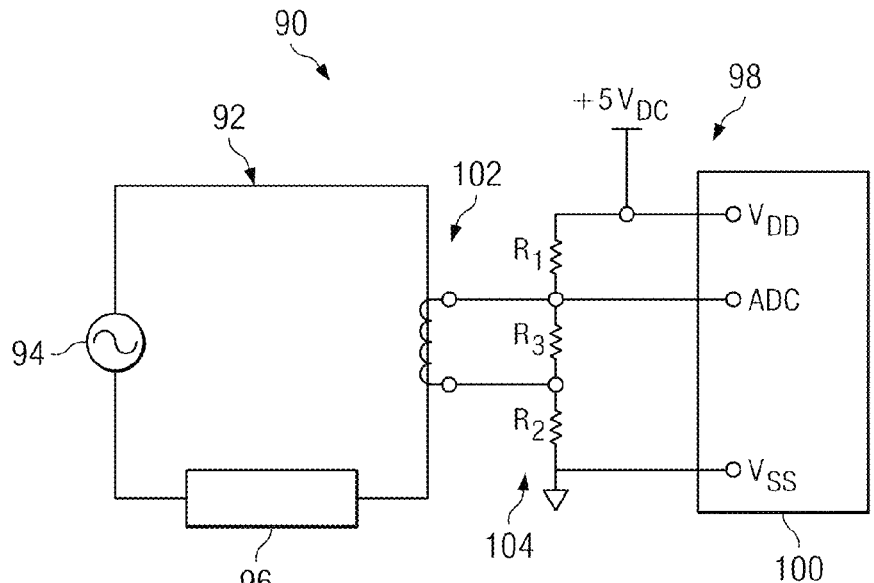
FIG. 5 schematically illustrates an example of an electrical circuit which may be utilized to measure a current waveform of an electrosurgical device.

An example for measuring current loads and for determining an instrument's ablative state is shown in the schematic illustration of circuit 90 in FIG. 5. As illustrated, an electrode circuit 92 powered by power supply 94, e.g., RF generator, may supply power to an electrode assembly which functions as an RF load 96. The electrode assembly is preferably disposed within an electrosurgical instrument as described above for ablating tissue regions of interest. A sensing circuit 98 may be in electrical communication with the electrode circuit 92 via a current sensing transformer 102 which may be utilized to allow direct measurements of the RF current waveform from circuit 92. The measured current may be converted to a digital signal by implementing a high-speed digital signal processing (DSP) and/or microcontroller (MCU) device 100 which is part of the sensing circuit 98.

The current measurement detected from transformer 102 may be input to a high-speed analog-to-digital converter (ADC) input on DSP 100, which may utilize this input signal to calculate the RMS and peak values of the waveform as well as to calculate the Crest Factor of the waveform. An example of a suitable DSP may include the Microchip dsPIC30 line of devices which provides a 10-bit converter resolution to represent the measured analog sample. Moreover, the Microchip dsPIC30 is widely available commercially and typically includes on-board ADC converters that operate at a throughput rate of up to 2 MSPS. A number of manufacturers also make DSP/MCU devices with similar capabilities that may be utilized. The example of the Microchip dsPIC30 is provided only to be illustrative of the type of DSP which may be utilized to process the various calculations and is not intended to be limiting in any manner.

With the sensed signals detected by transformer 102 input to the ADC input on DSP 100, several resistors 104 (e.g., R1, R2, and R3) connected to transformer 102 and also connected in series with DSP 100 may be included to provide sufficient resolution of the current waveform detected by transformer 102 and so that it is bounded by $V_{SS}$ (ground) and $V_{DD}$ (supply voltage) as shown in DSP 100 in the schematic illustration. Also, a sufficient DC bias may be added to the AC current waveform by the application of +5 $V_{DC}$ in communication with the resistors 104. If R1 and R2 were equal in the sensing circuit 98, the DC bias added to the current waveform may be about 2.5 $V_{DC}$.

With the electrode circuit 92 and sensing circuit 98 in electrical communication, the RMS value of the measured current may be computed based upon a predetermined number of samples, N, measured by current sensing transformer 102. Accordingly, the RMS value of N samples of a signal can be computed using the expression:

$$X_{RMS} = \sqrt{\frac{X_1^2 + X_2^2 + X_3^2 + \ldots + X_N^2}{N}} \quad (2)$$

The high-speed ADC on DSP 100 can be run at up to, e.g., 2 MSPS, for input sampling. The calculated RMS value may be fairly accurately calculated when, e.g., N=256 samples, are included in the function. The current waveform may be sampled by sensing circuit 98 at a frequency of:

$$f_{SAMPLE} = f_{SIGNAL}\left(1 - \frac{1}{N}\right) \quad (3)$$

where N=256 such that representative samples are collected over approximately 256 cycles. The value of $f_{SAMPLE}$ represents the sampling frequency by sensing circuit 98 while $f_{SIGNAL}$ represents the frequency of the measured signal through electrode circuit 92.

Figure 6:
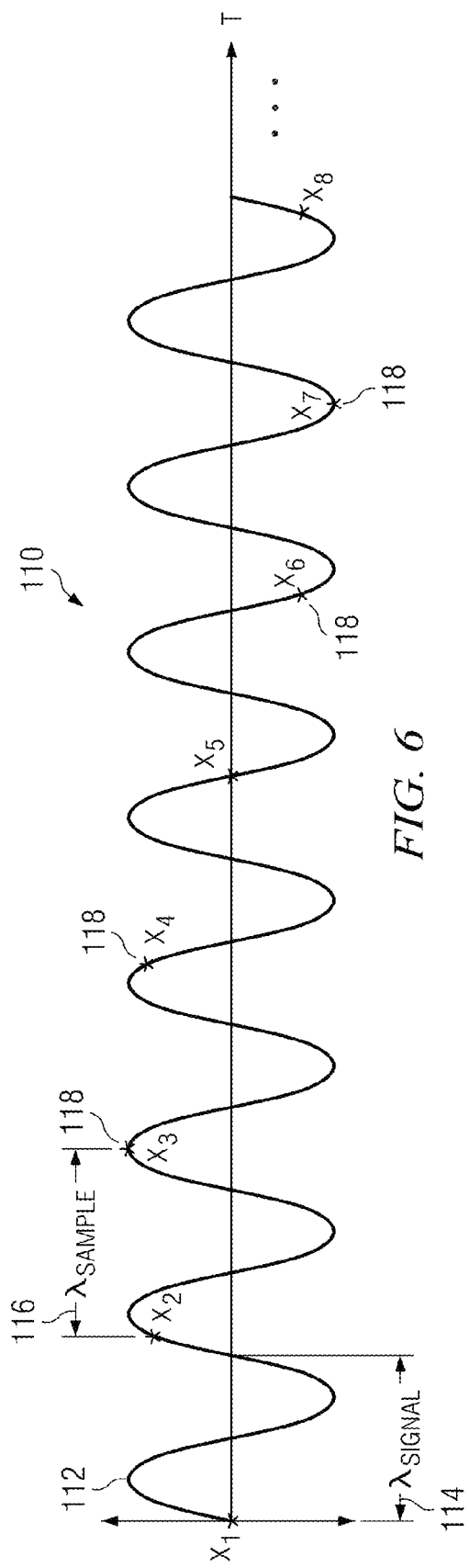
FIG. 6 shows a chart illustrating a current waveform in the form of a sine wave and the sampling period for obtaining measurements of the waveform.
Figure 7:
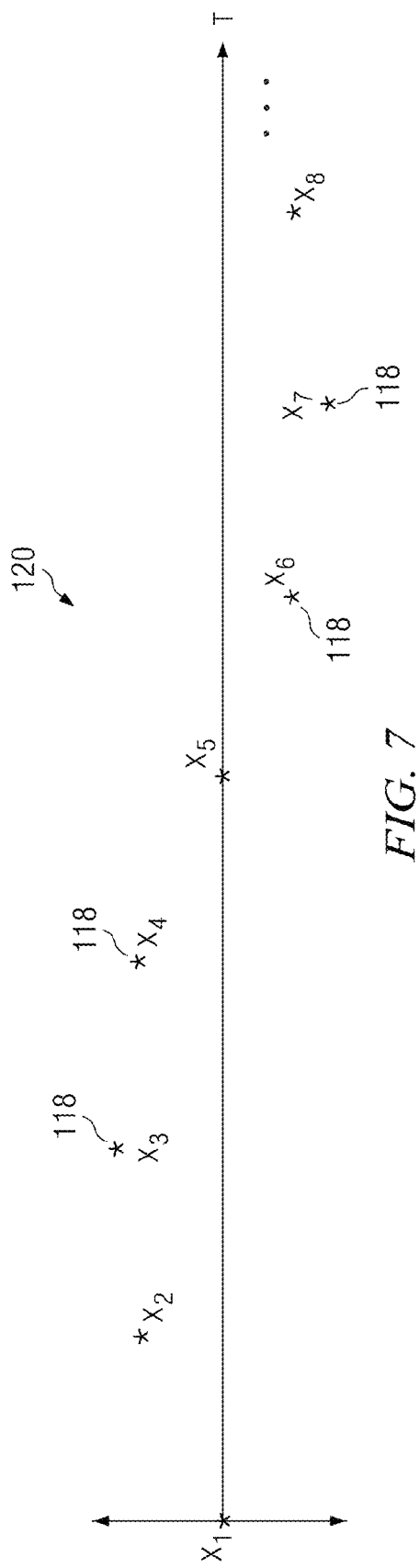
FIG. 7 illustrates the measured samples providing a reasonable approximation of the waveform.

This is shown in the graph 110 of FIG. 6 which illustrates the signal wavelength 114, $\lambda_{SIGNAL}$, and "wavelength" of the sampling rate 116, $\lambda_{SAMPLE}$, where the current signal through electrode circuit 92 is represented by sine wave 112 and the measured values 118 of $X_1, X_2, \ldots, X_8$ are measured at the frequency, $f_{SAMPLE}$, by sensing circuit 98. Considered together, this representative measurement of, e.g., eight samples $(X_1, X_2, \ldots, X_8)$, can provide a reasonable approximation of the wave shape, as shown in the plot 120 of FIG. 7. The representative measurement of eight samples is shown only for illustrative purposes and the number of samples may vary depending upon the sampling frequency and the sampling time.

With the N number of samples, e.g., N=256, a first step in the data processing is to subtract the DC bias from each of the N samples. For a 10-bit value, this would result in a signed value between −511 and 512. After the DC bias is removed, each of the samples may be scanned with the absolute value calculated and the maximum value identified and retained, which represents $X_{PEAK}$. DSP 100 may include at least two 40-bit accumulators and built in functions to perform algebraic operations which enable calculation of the numerator of the $X_{PEAK}$ value.

After the values of the samples, N, are squared and accumulated, they are divided by the N samples, e.g., 256 samples, and the square root of the resulting value is calculated to provide $X_{RMS}$ according to equation (2) above. With $X_{PEAK}$ and $X_{RMS}$ calculated, the Crest Factor, C, of the waveform may be calculated according to equation (1) above. This may allow for all three values: $X_{PEAK}$, $X_{RMS}$, and C to be reported via a user interface as an absolute limit or they may be used as input to either an RF or other control algorithm. For example, an algorithm may advantageously be used to regulate the vacuum or suction flow through the aspiration lumen in the device in order to allow the system to continuously remain in the ablative or plasma mode.

The Crest Factor, C, also may be used as an input for an indicator to determine whether the electrosurgical device is in a plasma mode (ablative) or a thermal mode (non-ablative), based on whether C has exceeded a specified threshold.

Figure 8:
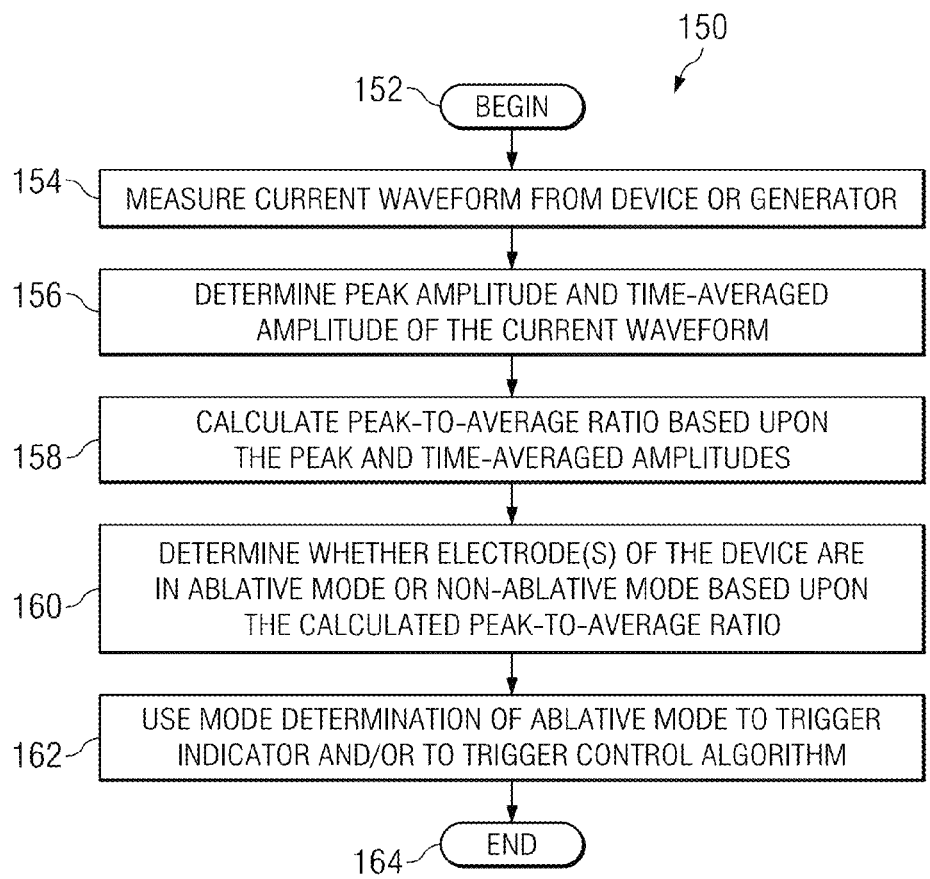
FIG. 8 shows a flow chart showing a method according to teachings of the present disclosure.

Now referring to FIG. 8, a flow diagram 150 showing a method according to the present disclosure is shown. The method 150 begins 152 as an electrosurgical device is used and the current waveform at the device or at the associated generator is measured 154. Next the peak amplitude and time-averaged amplitude of the current waveform is calculated 156. The peak-to-average ratio is then calculated 158 based upon the peak and time-averaged amplitudes determined in step 156. This peak-to-average ratio may then preferably be used to determine whether the electrosurgical is in an ablative mode or a non-ablative mode 160. When it is determined that the device is operating in an ablative mode, an indicator (such as indicator 55 shown in FIG. 2) may be illuminated or otherwise activated 162.

Alternatively, the indicator may be activated instead when a non-ablative mode or state is detected. In yet another embodiment, two or more indicators may be provided and each indicator may be activated to signal the detection of a selected mode of operation at the electrode. In still other alternative embodiments, the associated generator may include a visual or audible indicator in order to indicate the detected mode of operation of the electrode. In other embodiments, the determination that the device is in an ablative mode may be used as an input in a control algorithm as discussed above. In a preferred embodiment, steps 154, 156, 158, 160 and 162 may be continuously cycled while the electrosurgical device is activated, providing a real time or substantially real time indication of the ablative (or non-ablative) state of the electrosurgical device. The method ends at 164 when the electrosurgical device is inactive.

Other modifications and variations can be made to the disclosed embodiments without departing from the subject invention. For example, other uses or applications in characterizing waveforms are possible. Similarly, numerous other methods of controlling or characterizing instruments or otherwise treating tissue using electrosurgical probes will be apparent to the skilled artisan. Moreover, the instruments and methods described herein may be utilized in instruments for various regions of the body (e.g., shoulder, knee, etc.) and for other tissue treatment procedures (e.g., chondroplasty, menectomy, etc.). Thus, while the exemplary embodiments have been described in detail, by way of example and for clarity of understanding, a variety of changes, adaptations, and modifications will be obvious to those of skill in the art. Therefore, the scope of the present invention is limited solely by the appended claims.

What is claimed is:

1. A method of determining a mode of an electrosurgical instrument, comprising:
   supplying a first high frequency square waveform voltage input to the instrument;
   sensing a measured current waveform generated at an electrode of the instrument;
   determining a peak amplitude and a time-averaged amplitude of the measured current waveform;
   calculating a peak-to-average ratio based upon the peak and the time-averaged amplitudes; and determining whether the electrode of the instrument is in an ablative mode or non-ablative mode based upon the calculated peak-to-average ratio, wherein while supplying the first high frequency voltage input, the calculated peak-to-average ratio of the measured current waveform increases significantly when the instrument is in the ablative mode as compared to the non-ablative mode and wherein during the ablative mode a plasma is generated at the electrode.

2. The method of claim 1 further comprising activating an indicator disposed on the instrument when the instrument is determined to be operating in the ablative mode.

3. The method of claim 1 wherein the sensing of the measured current waveform comprises sensing the measured current waveform via a current sensing transformer.

4. The method of claim 3 further comprising adding a DC bias to the measured current waveform.

5. The method of claim 4 wherein calculating further comprises removing a DC bias from the measured current waveform.

6. The method of claim 1 wherein the calculating comprises calculating via a digital signal processor in electrical communication with the instrument.

7. The method of claim 1 further comprising sampling the measured current waveform at some frequency slightly below the fundamental frequency of the measured current waveform so that the sampling is performed over a multiple number of successive cycles of the measured current waveform.

8. The method of claim 1 wherein the measured current waveform is characterized by a spike at a leading edge of a half cycle followed by a relatively lower level for a remainder of the half cycle when the instrument is in the ablative mode.

9. The method of claim 1 wherein the peak-to-average ratio of the measured current waveform increases as an ablative load is applied by the instrument.

10. The method of claim 1 further comprising utilizing the peak-to-average ratio as an input for a control algorithm of the instrument.

11. The method of claim 1 wherein the peak-to-average ratio approximates the value 1 when in non-ablative mode.

12. The method of claim 1 wherein the measured current waveform is characterized by a square waveform when in non-ablative mode.

13. The method of claim 1 wherein during the step of supplying the first high frequency voltage input, the electrode of the instrument is initially in the non-ablative mode and transitions to the ablative mode as a plasma discharge is initiated.

14. The method of claim 1 wherein when the electrode is the non-ablative mode, the measured current waveform and the voltage waveform are similar in shape, and when the electrode is in the ablative mode, the measured current waveform and the voltage waveform look significantly dissimilar in shape.

15. A method of determining a state of an electrosurgical instrument, comprising:
    supplying a fixed high frequency square waveform voltage input to the instrument;
    sensing a measured current waveform generated at an electrode assembly of the instrument;
    determining a peak amplitude and a time-averaged amplitude of the measured current waveform;
    calculating a peak-to-average ratio based upon the peak and the time-averaged amplitudes; and
    determining whether the electrode assembly is generating a plasma, based upon the calculated peak-to-average ratio, wherein the initiation of the plasma at the electrode assembly causes the calculated peak-to-average ratio to increase significantly compared to when no plasma is present.

16. A method of determining a tissue effect mode of an electrosurgical instrument, comprising:
    supplying a high frequency square waveform voltage input to the instrument;
    sensing a measured current waveform generated at an electrode of the instrument;
    determining a peak amplitude and a time-averaged amplitude of the measured current waveform;
    calculating a peak-to-average ratio based upon the peak and the time-averaged amplitude; and
    wherein during the supplying step, the tissue effect mode at the electrode may transition between an ablative mode and non-ablative mode while continuing to maintain the high frequency square waveform voltage input; the tissue effect mode detected based upon the calculated peak-to-average ratio wherein the calculated peak-to-average ratio is significantly higher when the instrument is in the ablative mode as compared to the non-ablative mode.

* * * * *